US012578339B2

(12) United States Patent
Yozgat

(10) Patent No.: US 12,578,339 B2
(45) Date of Patent: Mar. 17, 2026

(54) HEXOKINASE 1 ISOFORM B FOR USE AS A PROGNOSIS MARKER AND SPECIFIC TARGET AGAINST CANCER

(71) Applicant: ISTANBUL MEDIPOL UNIVERSITESI, Istanbul (TR)

(72) Inventor: Yasemin Yozgat, Istanbul (TR)

( * ) Notice: Subject to any disclaimer, the term of this patent is extended or adjusted under 35 U.S.C. 154(b) by 1093 days.

(21) Appl. No.: 17/597,743

(22) PCT Filed: Jul. 19, 2020

(86) PCT No.: PCT/TR2020/050633
§ 371 (c)(1),
(2) Date: Jan. 21, 2022

(87) PCT Pub. No.: WO2021/015700
PCT Pub. Date: Jan. 28, 2021

(65) Prior Publication Data
US 2022/0260572 A1 Aug. 18, 2022

(30) Foreign Application Priority Data
Jul. 21, 2019 (TR) ................................. 2019/10857

(51) Int. Cl.
*G01N 33/574* (2006.01)
*C12N 15/113* (2010.01)
*G01N 33/573* (2006.01)

(52) U.S. Cl.
CPC ... *G01N 33/57423* (2013.01); *C12N 15/1137* (2013.01); *G01N 33/573* (2013.01); *G01N 33/57484* (2013.01); *C12Y 207/01001* (2013.01); *G01N 2333/91215* (2013.01); *G01N 2500/04* (2013.01)

(58) Field of Classification Search
CPC .................................................. C12N 15/1137
See application file for complete search history.

(56) References Cited

U.S. PATENT DOCUMENTS

2018/0303820 A1* 10/2018 Behar .................. A61K 31/496
2019/0231761 A1* 8/2019 Shen .................. C12N 15/1137

OTHER PUBLICATIONS

International Search Report for corresponding PCT/TR2020/050633, dated Oct. 26, 2020.
Written Opinion of the International Searching Authority for corresponding PCT/TR2020/050633. dated Oct. 26, 2020.
Yozgat, Y. "P53-Regulated Hexokinase 1b is a Novel Target for Metabolic Theraphy against Non-Small-Cell Lung Cancer". Thesis, Sabanci University, Jul. 19, 2019 (Jul. 19, 2019), Abstract.

* cited by examiner

*Primary Examiner* — Mark L Shibuya
(74) *Attorney, Agent, or Firm* — Egbert, McDaniel & Swartz, PLLC

(57) ABSTRACT
Disclosed is an isoform of hexokinase 1 (HK1), namely hexokinase 1b (HK1b), for use as a prognosis marker and as a specific target for use in treatment of cancer.

5 Claims, 21 Drawing Sheets

Specification includes a Sequence Listing.

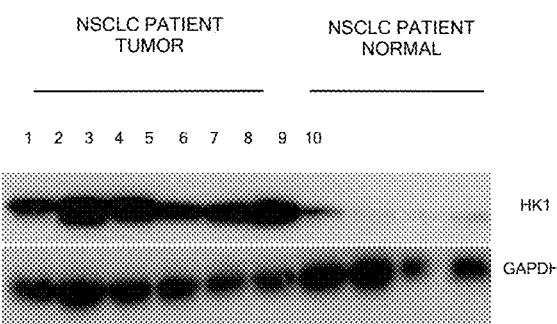
Fig. 1
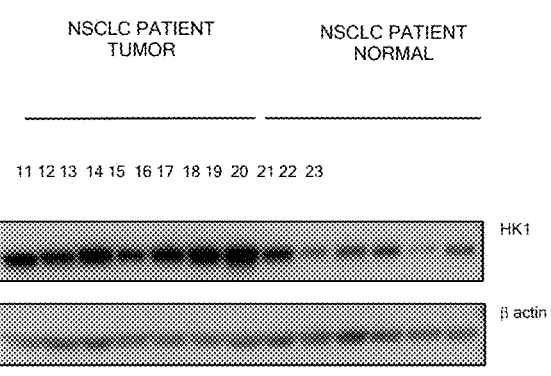
Fig. 2
Fig. 3

RMS fluctuation

HEXOKINASE 1 ISOFORM B FOR USE AS A PROGNOSIS MARKER AND SPECIFIC TARGET AGAINST CANCER

REFERENCE TO AN ELECTRONIC SEQUENCE LISTING

The contents of the electronic sequence listing (MEDI-POLPCT53-seq1-00001.txt; Size: 1,679 bytes; and Date of Creation: Jul. 21, 2019) is herein incorporated by reference in its entirety.

DESCRIPTION

Technical Field

This invention relates to an isoform of hexokinase 1 (HK1), namely hexokinase 1b (HK1b), for use as a prognosis marker and as a specific target for use in treatment of cancer.

Background of the Invention

In general terms, cancer is defined as the uncontrolled growth of cells. One of the distinct hallmarks of the cancer is metabolic reprogramming (1). Due to this ability, cancer cells, unlike normal cells, rely on increased glycolytic flux for their growth and proliferation and this in turn renders them more vulnerable to the disruption of glucose metabolism (2). Although development of new therapies for targeting altered glucose metabolism of cancer have found some success in preclinical, clinical success has been limited due to induced adverse side effects (3).

Deregulation of glycolysis is common in NSCLC (4). One of the important regulatory roles of $p^{53}$ is to control the cellular metabolism pathway by activating Hexokinases (HKs) to increase glycolysis depending on level of glucose and oxygen (5, 6). Hexokinases (HKs) catalyze the essentially irreversible first step of glucose metabolism in cells by phosphorylating glucose to glucose-6-phosphate (G-6-P).

The HK enzymes are encoded by four genes, HK1, HK2, HK3, and HK4. While HK1 is ubiquitously expressed in almost all mammalian tissues, HK2 is normally expressed in insulin-sensitive tissues such as adipose, skeletal, and cardiac muscles. HK3 is usually expressed at low levels, and HK4 expression is restricted to the pancreas and liver (7). Among these, HK1, HK2 and HK3 have a much lower Km value for glucose, suggesting higher affinity for glucose compared to HK4. However, HK1 is the only isoform that shows reduced inhibition by its product G6P in the presence of inorganic phosphate. Therefore, during periods of high energy demand, in which the intracellular concentration of Pi would typically increase while that of G6P decrease, the HK1 activity would increase, causing more glucose being phosphorylated by HK1 and entering downstream metabolism primarily for energy production. While HK1 is associated mainly with mitochondria, HK2 is associated with both mitochondria and cytoplasmic compartments (8,9, and 10).

Compared to HK2 gene where there is only one transcript, there are several transcripts of the HK1 gene due to the alternative splicing. Although we have increasing knowledge on transcript structures with the advent of the RNA sequencing technologies, we are still far from identifying the full landscape of the transcriptome. There are multiple gene annotation databases, and not all of them are consistent with each other. Here we use the RefSeq gene annotations, which is one of the largest resources for transcript definitions. According to the RefSeq gene annotations, there are 10 different isoforms of the HK1 gene. Half of these isoforms are specific to the testis tissue, and they are not observed in other tissues (11, 12). Differential expression patterns of the three of the remaining isoforms of HK1 that share high sequence and structural homology namely, HK1a, HK1b and HK1c have not been studied, and their role in tumorigenesis in NSCLC and other cancers, cell survival, and drug response is still elusive.

Herein the inventors aim to identify the isoform-specific contributors to cancer cell glucose metabolism that could be selectively targeted to eliminate cancer cells without compromising systemic homeostasis or corresponding metabolic functions in normal cells as this could be a very attractive approach for cancer therapy.

SUMMARY OF THE INVENTION

The present invention relates to HK1b and its role in tumorigenesis. In particular the present invention relates to a method for treating/preventing cancer, specifically non-small cell lung cancer (NSCLC).

Present invention is mainly based on the discovery that of the three HK1 isoforms, particularly HK1b and HK1c, only HK1b is predominantly expressed in A549 cells and NSCLC patient tumors, this distinguishes NSCLC cells from the normal surrounding lung cells and HK1b is associated with poor NSCLC patient survival. Furthermore, the inventors were able to show that HK1b expression was changed based on p53 status using p53 null and p53WT NSCLC cells. In order to identify the mechanisms of HK1b regulation by p53, p53 and HK1b isoform were deleted in human NSCLC A549 cells using CRISPR/Cas9 system and showed that p53 positively regulates HK1b. Experiments carried out on HK1b knock out of human A549 cells (A549HK1b$^{-/-}$) and showed that HK1b inhibits proliferation and in vivo tumor growth of NSCLC cells.

In order to prepare an HK1b knock out, double stranded molecules comprising a sense strand and an anti-sense strand were prepared wherein the sense strand comprises a nucleotide sequence corresponding to SEQ ID No: 1, SEQ ID No: 2 or SEQ ID No: 3 and accordingly the anti-sense strand for these sense strands comprises a nucleotide sequence corresponding to SEQ ID No: 4, SEQ ID No:5 and SEQ ID No:6 respectively. Further these sense and anti-sense strands hybridize with each other to form the double stranded molecule. For example, sense strand comprising SEQ ID No:1 hybridizes with its anti-sense strand shown with SEQ ID No: 4 (double stranded molecule 1) and sense strand comprising SEQ ID No:2 hybridizes with its anti-sense strand SEQ ID No:5 (double stranded molecule 2), and sense strand comprising SEQ ID NO: 3 hybridizes with its antisense strand SEQ ID No: 6 (double stranded molecule 3).

In one aspect, an object of the invention is to provide isolated double stranded molecules that, when introduced into a cell knocks out HK1b and as a result inhibits glycolysis and proliferation and growth of cancer cells, particularly NSCLC cells.

Another object of the invention is to provide isolated double stranded molecules for use as a drug, preferably for use in a method for treatment of cancer, particularly NSCLC.

Another object of the invention is to provide compositions for either or both of the treatment or prevention of an HK1b-associated disease such as cancer, specifically NSCLC, wherein such compositions comprise at least one of the double stranded molecules 1, 2 or 3 of the present invention.

Another object of the invention is to provide a method for detecting or diagnosing cancer, specifically NSCLC, in a subject using as an index the expression level of HK1b isoform. More particularly, an increase in the level of HK1b isoform in a subject derived biological sample compared to a normal control level of test isoform indicates the presence on cancer in the subject or indicates that the subject suffers from cancer, for example NSCLC.

A further object of the invention is to provide a method of screening for a candidate substance for prevention and/or treatment of an HK1b-associated disease, such as cancer, specifically NSCLC. As such, the candidate substance can be selected using as an index; (i) the binding activity to the HK1b isoform or (ii) the inhibitory activity against a biological activity of HK1b isoform or (iii) the suppressing activity against the expression of HK1b isoform. The biological activities of the HK1b isoform that are of particular interest to the screening method of the present invention comprise glycolysis.

A series of objectives are set forth above. It would be understood by a person skilled in the art that one or more embodiments of the invention can meet certain objectives alone or in combination with one another.

BRIEF DESCRIPTION OF THE DRAWINGS

FIGS. 1-7 demonstrates the over-expression of HK1 in clinical Non small lung cancers (NSCLC). FIG. 1 and FIG. 2 depicts the protein levels of HK1 in two different western blot analyses with total 13 NSCLC patient tumor cases and 10 non-adjacent normal lung.

FIG. 3 depicts quantification of HK1 levels in NSCLC tumor (n=13) and normal lung samples (n=10), showing that HK1 expression is significantly elevated (p<0.0001). FIG. 4 depicts the in situ expression of HK1 using the immunohistochemistry assay. All the noncancerous epithelium showed weak staining of HK1, while tumor cells showed moderate to strong staining of HK1 FIG. 5 depicts comparison analysis between NSCLC and normal samples in GSE31210 dataset by using the Gene Set Enrichment Analysis (GSEA) based on p53 gene signature expression (p53 WT and p53mutant) showing that patients with mutant p53 express higher levels of HK1. FIG. 6 depicts comparison analysis between NSCLC and normal samples in GSE31210 dataset by using the Gene Set Enrichment Analysis (GSEA) of stage I and II patients showing that stage II patients have higher HK1 expression only in p53 WT group. FIG. 7 depicts survival analysis showing that higher expression of HK1 was associated with decreased relapse-free survival (P=0.01), suggesting that higher HK1 expression is associated with disease progression. For statistical analysis, Student's t-test (**P<0.05) were performed.

FIG. 8 depicts the RefSeq gene annotations of tissue specific differential three HK1 isoforms: HK1a, HK1b and HK1c and one transcript of HK2 gene. HK1a transcript contains different exons at the 5' end and therefore it is possible to differentiate this transcript Both Hk1b and HK1a isoforms possess one extra exon, exon 8, which is missing in the HK1c isoform. FIG. 9 depicts structural alignment between crystal structures of HK1b and HK1c model. The extra exon in HK1b, which is shown in blue, codes for 32-amino acid long alpha-helix that is part of the small sub-domain of N-terminus. For the sake of simplicity only one monomer is shown.

FIG. 10 depicts root-mean-square-fluctuation analysis which was performed using the trajectories of HK1 b, c isoforms and HK2 and showed that HK1b isoform contained unique sequences that might mediate the stability of N-domain.

FIG. 11 shows representative semi q-PCR amplification results for HK1 isoforms, HK2 and P53 in H1299 and A549 cells. FIG. 12 shows immunoblot analysis of HK1 and HK2 in A549 and H1299 cells. FIG. 13 shows representative semi q-PCR amplification results for HK1 isoforms, HK2 and P53 in NSCLC patient tumors (n=3). FIG. 14 shows RNA was extracted from NSCLC patient normal lung and tumor samples, HK1b, HK1c, HK2 (normal n=6, tumor n=6) and p53 (normal n=7, tumor n=7) levels were determined by qRT-PCR. mRNA levels were normalized to ACTB mRNA. Data are from two or three independent experiment as triplicate, presented as mean±SEM, Student's t-test FIG. 15 depicts Kaplan-Meier plots showing the association of HK1b isoform overexpression between normal and TCGA Lung adenocarcinoma samples in patients from the TCGA cohort FIG. 16 depicts Kaplan-Meier survival curves for adenocarcinoma (n=501). FIG. 17 depicts Kaplan-Meier survival curves for squamous cell carcinoma (n=489). For these tests patients stratified according to low or high HK1b expression levels. P values indicate significance levels from the comparison of survival curves using the Log-rank (Mantel-Cox) test FIG. 18-20 demonstrates the effect of genetically disrupt HK1b isoform depletion on tumorigenesis and metabolism of NSCLC cells using CRISPR/Cas9 system and knockdown by same CRISPR sequence by siRNA.

FIG. 21 depicts the results of analysis of the mitochondrial respiration rate following HK1b knockout (KO) showed not significant change in oxygen consumption rate (OCR) and respiration. FIG. 22 depict the results of measuring extracellular acidification rate (ECAR) using the XF glycolysis stress test and the XF glycolytic rate assay showing that significant reductions in glycolytic activity in A549 cells upon HK1b isoform loss (A549 HK1b−/−) compared to control cells (A549 WT) (p=0.0001 and p=0.002, respectively). FIG. 23 depicts the results of in vitro, flow cytometry analyses of Ki67, a marker for proliferation, was performed and A549 HK1b−/− cells showed an approximately 35% decrease of Ki-67 level.

In FIG. 24 A549 WT or A549 HK1b−/− cells were intra-tracheally injected into immunodeficient NSG male mice. Graphs on the left show tumor volume in (n=7, each) A549 WT (control) and A549 HK1b–/– (n=7) mouse and representative images of resected tumors on the left Tumor volumes presented as mean±SEM, two-tailed unpaired t-test FIG. 25 depicts immunohistochemical staining of HK1 expression and H&E staining in representative mouse xenograft A549WT tumor (left) and A549 HK1b–/– tumor (right). Images are 40× magnification; insets are 200× magnification. Scale bars, 100 μm.

DETAILED DESCRIPTION OF THE INVENTION

Figure 4:
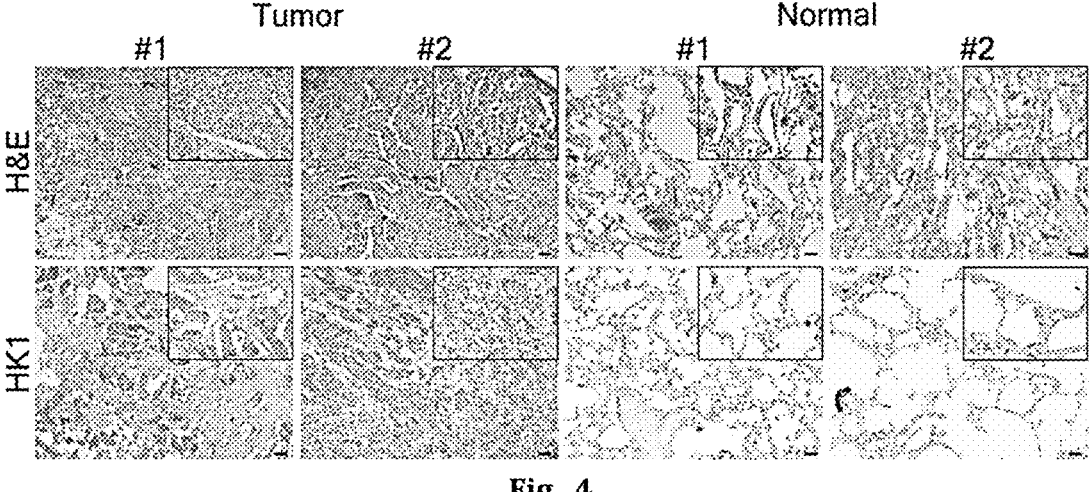

An embodiment of the invention is a method to detect or diagnose cancer in a subject, said method comprising determining en expression level of HK1b isoform in a subject derived biological sample, wherein an increase of said level compared to normal control level of said isoform indicates that said subject suffers from developing cancer, wherein the expression level is determined by immunoblotting followed by quantification of the band intensities with densitometry. Densitometry methods are well known for a person skilled in the art, for example for densitometry a software such as ImageJ or Quantity One can be used.

In a preferred embodiment, at least 10% or more increase in the expression level of HK1b isoform in a subject derived sample is considered as an increased level.

In a preferred embodiment, a subject derived biological sample comprises a biopsy specimen, saliva, sputum, blood, serum, plasma, pleural effusion or urine.

In a preferred embodiment, cancer is NSCLC.

Another embodiment of the invention is a method of screening for a candidate substance for use in treatment of cancer or the inhibition of cell growth (Method 1) said method comprising the steps of:
  (a) contacting a test substance with HK1b isoform (SEQ ID No: 7 and SEQ ID No:8) or functional equivalent thereof;
  (b) detecting the binding activity between the HK1b isoform (SEQ ID No: 7 and SEQ ID No:8) or functional equivalent thereof and the test substance; and
  (c) selecting the test substance that binds to the HK1b isoform (SEQ ID No: 7 and SEQ ID No:8) or functional equivalent thereof.

Another embodiment of the invention is a method of screening for a candidate substance for use in treatment of cancer or the inhibition of cell growth (Method 2) said method comprising the steps of:
  (a) contacting a test substance with HK1b isoform (SEQ ID No: 7 and SEQ ID No:8) or functional equivalent thereof;
  (b) detecting the biological activity of the HK1b isoform (SEQ ID No: 7 and SEQ ID No:8) or functional equivalent thereof in (a); and
  (c) selecting the test substance that suppresses the biological activity of HK1b isoform (SEQ ID No: 7 and SEQ ID No:8) or functional equivalent thereof in comparison with the biological activity detected in the absence of the test substance.

In Method 2 of the invention the biological activity is glycolysis.

In another embodiment, the present invention relates to double stranded molecules comprising a sense strand and an antisense strand, wherein the sense strand comprises a nucleotide sequence corresponding to SEQ ID No:1 and an antisense strand comprises a nucleotide sequence corresponding to SEQ ID No:4, wherein said sense strand and antisense strand hybridize to each other to form a double stranded molecule and wherein the said double stranded molecule, when introduced into a cell expressing HK1b isoform, inhibits the expression of HK1b isoform.

In another embodiment, the present invention relates to double stranded molecules comprising a sense strand and an antisense strand, wherein the sense strand comprises a nucleotide sequence corresponding to SEQ ID No:2 and an antisense strand comprises a nucleotide sequence corresponding to SEQ ID No:5, wherein said sense strand and antisense strand hybridize to each other to form a double stranded molecule and wherein the said double stranded molecule, when introduced into a cell expressing HK1b isoform, inhibits the expression of HK1b isoform.

In another embodiment, the present invention relates to double stranded molecules comprising a sense strand and an antisense strand, wherein the sense strand comprises a nucleotide sequence corresponding to SEQ ID No:3 and an antisense strand comprises a nucleotide sequence corresponding to SEQ ID No:6, wherein said sense strand and antisense strand hybridize to each other to form a double stranded molecule and wherein the said double stranded molecule, when introduced into a cell expressing HK1b isoform, inhibits the expression of HK1b isoform.

A method for prophylaxis and/or treatment of cancer in a subject said method comprises administering to said subject a pharmaceutically effective amount of a double-stranded molecule against HK1b isoform.

An embodiment of the invention relates to a double stranded molecule comprising a sense strand of SEQ ID No:1 and an antisense strand of SEQ ID no: 4 for use as a medicament, preferably for use in prophylaxis and/or treatment of cancer.

An embodiment of the invention relates to a double stranded molecule comprising a sense strand of SEQ ID No:2 and an antisense strand of SEQ ID no: 5 for use as a medicament, preferably for use in prophylaxis and/or treatment of cancer.

An embodiment of the invention relates to a double stranded molecule comprising a sense strand of SEQ ID No:3 and an antisense strand of SEQ ID no:6 for use as a medicament, preferably for use in prophylaxis and/or treatment of cancer.

A method for prophylaxis and/or treatment of cancer in a subject said method comprises administering to the subject a pharmaceutically effective amount of a double-stranded molecule against HK1b isoform in combination with a chemotherapy agent selected from a group comprising cisplatin, carboplatin, oxaliplatin.

Another embodiment of the invention relates to a pharmaceutical composition comprising; a double stranded molecule comprising a sense strand of SEQ ID No:1 and an antisense strand of SEQ ID no: 4 or a double stranded molecule comprising a sense strand of SEQ ID No:2 and an antisense strand of SEQ ID no: 5 or a double stranded molecule comprising a sense strand of SEQ ID No:3 and an antisense strand of SEQ ID no:6 and at least one pharmaceutically acceptable excipient wherein the double stranded molecule inhibits glycolysis and the expression of HK1b isoform when introduced into a cell expressing HK1b isoform.

Definitions

The words "a", "an", and "the" as used herein mean "at least one" unless otherwise specifically indicated.

The term "amino acid" refers to naturally occurring and synthetic amino acids, as well as amino acid analogs and amino acid mimetics that similarly functions to the naturally occurring amino acids.

Amino acids may be referred to herein by their commonly known three letter symbols or the one-letter symbols recommended by the IUPAC-IUB Biochemical Nomenclature Commission.

The terms "gene", "polynucleotides", "oligonucleotide", "nucleic acids", and "nucleic acid molecules" are used interchangeably unless otherwise specifically indicated and, similarly to the amino acids, are referred to by their commonly accepted single-letter codes. Similar to the amino acids, they encompass both naturally-occurring and non-naturally occurring nucleic acid polymers. The polynucleotide, oligonucleotide, nucleotides, nucleic acids, or nucleic acid molecules may be composed of DNA, RNA or a combination thereof.

In the context of the present invention, the phrase "HK1b isoform" encompasses polynucleotides that encode human HK1b isoform or any of the functional equivalents of the human HK1b isoform. In the present invention the HK1b isoform or a functional equivalent thereof can be obtained from nature as naturally occurring proteins via conventional cloning methods or through chemical synthesis based on the selected nucleotide sequence (e.g. SEQ ID No: 7 and SEQ ID No:8)

The terms "isolated" or "purified" used in relation to a substance (e.g., polypeptide, antibody, polynucleotide, etc.) indicate that the substance is removed from its original environment (e.g., the natural environment if naturally occurring) and thus altered from its natural state.

An "isolated" or "purified" antibody refers to antibodies that are substantially free of cellular material for example, carbohydrate, lipid, or other contaminating proteins from the cell or tissue source from which the protein (antibody) is derived, or substantially free of chemical precursors or other chemicals when chemically synthesized.

As used herein, the term "biological sample" refers to a whole organism or a subset of its tissues, cells or component parts (e.g., body fluids, including but not limited to blood, mucus, lymphatic fluid, synovial fluid, cerebrospinal fluid, saliva, amniotic fluid, amniotic cord blood, urine, vaginal fluid and semen). "Biological sample" further refers to a homogenate, lysate, extract, cell culture or tissue culture prepared from a whole organism or a subset of its cells, tissues or component parts, or a fraction or portion thereof. Lastly, "biological sample" refers to a medium, for example, a nutrient broth or gel in which an organism has been propagated, which contains cellular components, for example, proteins or polynucleotides. In the context of the present invention, a biological sample may preferably contain tissues or cells extracted from the lung, cervix, bladder, esophagus, or prostate, or an osteosarcoma or soft tissue tumor.

Unless otherwise defined, the term "cancer" refers to cancers over-expressing the HK1b isoform.

Herein the term "prophylaxis" refers to to any activity that reduces the burden of mortality or morbidity from disease. Prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis can include a wide range of prophylactic therapies aimed at alleviating the severity of the particular disorder, e.g. reducing the proliferation and metastasis of tumors.

To the extent that certain embodiments of the present invention encompass the treatment and/or prophylaxis of cancer and/or the prevention of postoperative recurrence, such methods may include any of the following steps: the surgical removal of cancer cells, the inhibition of the growth of cancerous cells, the involution or regression of a tumor, the induction of remission and suppression of occurrence of cancer, the tumor regression, and the reduction or inhibition of metastasis. Effective treatment and/or the prophylaxis of cancer decreases mortality and improves the prognosis of individuals having cancer, decreases the levels of tumor markers in the blood, and alleviates detectable symptoms accompanying cancer. A treatment may also deemed "efficacious" if it leads to clinical benefit such as, reduction in expression of the HK1b isoform, or a decrease in size, prevalence, or metastatic potential of the cancer in the subject.

In an aspect, a sense strand of a double helix molecule named as SEQ ID No:1 has the following sequence; AAGCGAUUUAAAGCGAGCGGAUU.

In an aspect, a sense strand of a double helix molecule named as SEQ ID No:2 has the following sequence; AAAGCGAUUUAAAGCGAGCGGUU.

In an aspect, a sense strand of a double helix molecule named as SEQ ID No:3 has the following sequence; GCGAUUUAAAGCGAGCGGAGUU.

In an aspect, an antisense strand of a double helix molecule named as SEQ ID No:4 has the following sequence; UCCGCUCGCUUUAAAUCGCUUUU.

In an aspect, an antisense strand of a double helix molecule named as SEQ ID No:5 has the following sequence; CCGCUCGCUUUAAAUCGCUUUUU.

In an aspect, an antisense strand of a double helix molecule named as SEQ ID No:6 has the following sequence; AAAGCGAUUUAAAGCGAGCGGUU.

In an aspect, a sense strand of a HK1b isoform, which is a double helix molecule, named as SEQ ID No:7 has the following amino acid sequence; GCGATTTAAAGCGAGCGGAG.

In an aspect, an antisense strand of a HK1b isoform, which is a double helix molecule, named as SEQ ID No:8 has the following amino acid sequence; CTCCGCTCGCTTTAAATCGC.

The invention will now be described with the following examples given purely as a means for exemplifying the scope of the present invention, therefore it is to be understood that the present invention is not limited to the particular sizes, shapes, dimensions, materials, methodologies, protocols, etc. described herein, as these may vary in accordance with routine experimentation and optimization.

It is also to be understood that the terminology used in the description is for the purpose of describing the particular versions or embodiments only, and is not intended to limit the scope of the present invention which will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

Unless otherwise defined, all technical and scientific terms used herein have the same meaning as commonly understood by one of ordinary skill in the art to which the present invention belongs. Although methods and materials similar or equivalent to those described herein can be used in the practice or testing of the present invention, suitable methods and materials are described below.

In addition, the materials, methods, and examples are illustrative only and not intended to be limiting.

10

Examples

1) Materials and Method a) Cell Culture and Treatment

Human non-small cell lung cancer (NSCLC) cell lines, including A549, H1299, were obtained from Dr. Engin Ulukaya's laboratory (University of Istinye) and propagated in monolayer culture in RPMI 1640 supplemented with 10% FBS, 1% penicillin-streptomycin, and 1% L-glutamine. All cells were maintained in a humidified atmosphere containing 5% $CO_2$ at 37 C. All cell lines were tested for *Mycoplasma* routinely every 3 months using MycoProbe *Mycoplasma* Detection Kit (R&D Systems). All cell lines were used between 10 passages window.

B) Gene Knockout and Knockdown in Lung Cancer Cells

A549-HK1b isoform-knockout cells were generated by using the CRISPR/Cas9 genome editing system. Briefly, the sgRNAs specific for HK1b isoform only was designed to target the eighth exon of human HK1 gene. pX458 vector with GFP selection marker from addgene, as described previously [19], was used to deliver Cas9 and a sgRNA targeting HK1b (namely sgHK1b) into the target cells.

The CRISPR guide sequences targeting HK1b were;

```
sense: GCGATTTAAAGCGAGCGGAG antisense: CTCCGCTCGCTTTAAATCGC
```

The expression of GFP sorted single-cell clones expressing sgHK1b were screened for p53 or HK1b isoform elimination and specific indel mutations at target loci was confirmed with PCR, DNA fragmentation analyses, and Sanger sequencing.

For siRNA-mediated gene knockdown, three different siRNA oligos targeting the HK1b were designed to target the eighth exon of human HK1 gene as follows:

```
siRNA#1
sense: AAGCGAUUUAAAGCGAGCGGAUU antisense: UCCGCUCGCUUUAAAUCGCUUUU siRNA#2
sense: AAAGCGAUUUAAAGCGAGCGGUU antisense: CCGCUCGCUUUAAAUCGCUUUUU siCRISPR (siRNA#3)
sense: GCGAUUUAAAGCGAGCGGAGUU antisense: CUCCGCUCGCUUUAAAUCGCUU
```

For functional ablation experiments, equal number of cells ($1\times10^5$) was plated and for the transient knockdown, cells were transfected with siRNA duplexes by a reverse transfection method using Lipofectoamine RNAiMAX (Life Technologies). Cells were harvested 48 hours later for qRT-PCR for transcriptional analyzing.

C) Patient Tissue Collection and Immunohistochemical Staining

This study was approved by the Ethics Committee of Istanbul Medipol University. 18 cases of clinically and immunohistologically verified NSCLC primary tumor and normal lung tissues were collected from affiliated hospital of Istanbul Medipol University (Istanbul, Turkey), and were agreed by all patients. The patients' attributes are shown in Table 1. The sections were stained with indicated antibodies, and staining of HK1, p53, and Ki-67 was scored pathologists based on the percentage of positive cells and staining intensity. Patients' clinical characteristics are listed in Table 1.

| Patient # | Gender Age | (Years) | Histological type | Grade | Stage | p53 | Used in experiment |
|---|---|---|---|---|---|---|---|
| 1 | Male | 64 | ADC | 2 | pT2aN1 | pozitif (%95) | WB |
| 2 | Male | 67 | ADC | 3 | pT3N0 | negatif (%1) | WB |
| 3 | Female | 75 | ADC | 2 | pT1bN0 | negatif (%1) | WB |
| 4 | Male | 68 | ADC | 3 | pT2bN1 | pozitif (%90) | WB,q-PCR |
| 5 | Female | 53 | ADC | 1 | pT2aN0 | negatif (%1) | IHC,WB,q-RT |
| 6 | Male | 54 | ADC | 3 | pT2aN2 | negatif (%0) | IHC,WB,q-RT |
| 7 | Male | 54 | ADC | 3 | pT3N0 | negatif (%1) | WB,q-RT |
| 8 | Male | 62 | Solid ADC | 3 | ypT2bN0 | pozitif (%95) | IHC,WB |
| 9 | Male | 66 | Enteric type ADC | 2 | pT1aN1 | negatif (%0) | IHC,WB |
| 10 | Male | 65 | Invasive mucinous ADC | 1 | pT4N1 | negatif (%0) | IHC,WB |
| 11 | Male | 66 | Enteric type ADC | 2 | pT2bN0 | pozitif (%95) | IHC,WB |
| 12 | Male | 72 | Acinar dominant type ADC | 2 | pT2N1 | pozitif (%90) | WB |
| 13 | Male | 68 | Solid ADC | 3 | pT2N1 | pozitif (%90) | IHC,WB,q-RT |
| 14 | Female | 76 | Acinar dominant type ADC | 2 | pT2aN0 | negatif (%0) | WB |
| 15 | Male | 48 | Enteric type ADC | 2 | pT2aN1 | negatif (%0) | IHC,WB,q-RT |
| 16 | Male | 62 | Basaloid SCC | 2 | pT3N0 | pozitif (%100) | WB,q-RT |
| 17 | Male | 40 | SCC | 3 | pT2aN2 | negatif (%1) | WB,q-RT |
| 18 | Male | 69 | Solid ADC | 3 | pT2aN1 | negatif (%0) | IHC |

D) the Cancer Genome Atlas NSCLC Cohort Analyses

Publicly available The Cancer Genome Atlas (TCGA) RNA-seq data on adenocarcinoma (n=511) and SCC (n ¼ 501) was used as an external cohort to verify DEGs between adenocarcinoma and SCC based on the RG cohort and to further analyze the expression of the HK1b isoform (transcript variant-8) between normal and TCGA Lung adenocarcinoma samples (RefSeq id NM_001322366). Lung Adenocarcinoma project contains 426 RNA sequencing of lung tumor tissues and matched with 602 normal lung tissues from the GTEx Project. For each database the supplied expected transcript read counts that are generated using the RSEM software package is used for the comparison. The read counts are normalized using the DESeq2 variance stabilized normalization method.

E) RNA Isolation and Quantitative PCR

RNA was isolated from human NSCLC cells and human clinical NSCLC tumor and normal samples by homogenization in Trizol reagent (Invitrogen) according to the manufacturer's instructions, followed by purification on an RNeasy column (Qiagen). RNA purity was assessed by Thermo NanoDrop 2000 (Thermo Fisher Scientific, Inc.) by standard absorbance ratios as $A260/A280 \geq 1.8$ and $A260/A230 \geq 1.5$. Complementary DNAs were synthesized from 2 g of total RNA using RevertAid First Strand cDNA Synthesis Kit (Thermo Fisher Scientific, Inc.) Real time Quantitative PCR (RT-qPCR) results obtained with Bio-Rad's iTaq Universal SYBR Green Supermix. The threshold cycle (Ct) for individual reactions were identified using iCycler IQ sequence analysis software (Bio-Rad). 3-actin was used for normalization of the data. All experiments were performed in triplicate.

The following primers were used in this study with the following sequences:

```
HK1a isoform:
Fwd., 5'-TGCCAAGCCCTGTTCTATGC-3',

Rev., 5'-CTGGGTCTTGAACGCACTG-3';

HK1b isoform:
Fwd., 5'-CGCTGAAGACCCAGATTGACA-3',

Rev, 5'-GCACCCGCAGAATTCGAAAG-3';

HK1c isoform:
Fwd, 5'-GCTGAGTGCCTGGGAGATTT-3',
```

```
-continued
Rev., 5'-TGGCATCATAGTCCTCATCTATTT-3',

HK2:
Fwd, 5'-CAACTTCCGTGTGCTTTGGG-3',

Rev., 5'-TGAGACCAGGAAACTCTCGT-3', p53
Fwd, 5'-GGAGCACTAAGCGAGCACTG

Rev., 5'-TCTCGGAACATCTCGAAGCG-3',

H_β-actin
Fwd, 5'-AGAGCTACGAGCTGCCTGAC-3'

Rev., 5'-AGCACTGTGTTGGCGTACAG-3'.
```

F) Reagents and Antibodies

Rabbit monoclonal primary antibodies against HK1 (C35C4), HK2 (C64G5), Phospho-Akt (Ser 473), total Akt, Phospho-STAT3(Tyr705), total STAT3, Cleaved PARP (Asp214) (D64E10), PARP (46D11), Cleaved Caspase-3 (Asp175) (5A1E), Caspase-3 (D3R6Y), Phospho-GSK-3β (Ser9) (D85E12), total GSK-3p (D5C5Z), Phospho-p53 (Ser15), Phospho-mTOR (Ser2448) (D9C2), Phospho-AMPKα (Thr172) (D4D6D), total AMPKα (D63G4), Atg13 (E1Y9V), β-Actin (13E5), and horseradish peroxidase (HRP)-conjugated rabbit and mouse secondary antibodies purchased from Cell Signaling Technologies (USA). Mouse monoclonal primary antibodies against p53 (DO-1), Bcl-2 (C-2), MAP LC3 (G-2), and BECN1 Antibody (G-11) purchased from Santa Cruz Biotechnologies (USA). Cisplatin (50 mg/100 mL) was purchased from Koçak Farma.

G) Cell Viability Assay

Twenty-four hours following seeding (15,000 cells/well) in a 96-well plate, A549 and A549 HK1b$^{-/-}$ cells (70%-80% confluent) were treated with vehicle (PBS/Saline), or cisplatin with concentrations range from 0-100 μM/ml and the cells incubated for a further 48 h. The cell viability was determined using the CellTiter-Blue assay kit (Promega) according to the manufacturer's instructions and absorbance measured at 595 nm with a microplate reader (Model 3550, Bio-Rad Laboratories, CA, USA). $IC_{50}$ was defined as the concentration causing a 50% reduction in absorbance relative to the negative control. $IC_{50}$ was determined by nonlinear regression analysis using Graphpad Prism v8 (Graphpad Software, CA, USA).

IC50 concentration of cisplatin are used in A549 (75 μM) and A549 HK1b$^{-/-}$ (47 μM) cells and after 48 hrs treatment cells were harvested by trypsinization, collected by centrifugation, washed once with 1 ml of PBS and stained with propidium iodide (BD Biosciences) according to the manufacturers' protocol and number of death cells was measured using fluorescence-activated cell sorting.

H) Cell Proliferation by FACS Analysis

A549 and A549 HK1b$^{-/-}$ cells were trypsinized and harvested at 50%-70% confluency. Cells were fixed with ice-cold 70% ethanol dropwise while vortexing and incubated at minus 20 degree for a minimum of 24 hr. Fixed cells were pelleted and washed twice with PBS. Anti-Human Ki-67, FITC kit is used to stain cells according to the manufacturers' protocol (BD Biosciences), Cells were analyzed with a FACS AriaII flow cytometer and processed using FlowJo software.

I) Western Blot Analysis

Cells were harvested and washed in PBS solution, collected, and then subjected to lysis in RIPA buffer containing proteinase inhibitor cocktail and phosphatase inhibitor cocktail (Roche). The lysates were subjected to centrifugation at 10,000 g at 4 C for 20 minutes and the supernatants removed. The total protein (50 g) was fractioned by 10% SDS-PAGE and electrophoretically transferred to Immobilon-FL PVDF membranes. The membrane was blocked with blocking buffer (Li-Cor) at room temperature for 1 hour, and then incubated with appropriate primary antibody at 4 C overnight. After washing with PBS containing 0.05% Tween 2 (PBST), the membrane was incubated with 1:2500 dilutions of appropriate secondary antibody for 2 hours at room temperature. The membrane was washed with PBST again, and Pierce ECL Western Blotting Substrate (Thermo Scientific) was used for development of immunoreactive bands. For immunoblotting of tissue samples, proteins were extracted from tumor and adjacent non-tumor lung samples collected from human NSCLC patients, snap frozen in liquid nitrogen, and stored at −80° C. Then protein lysis buffer (described above) was added to samples. Samples were vortexed, homogenized and subjected to three freeze/thaw cycles in dry ice, centrifuged and supernatant collected, and stored at −80° C. for subsequent immunoblotting.

J) Measurement of oxygen consumption rate and extracellular acidification rates

For Seahorse XFe96 assays, cells were seeded at pre-optimized final concentration $1.5 \times 10^4$ cells/well onto Seahorse XF-96-well plates and Glycolytic rate, Glycolysis stress and Mito Stress Tests were performed following the manufacturer's specifications (Seahorse Bioscience, North Billerica, MA). Each datum was determined minimally in triplicate. OCR and ECAR were reported as absolute rates (pmoles/min for OCR and mpH/min for ECAR) or normalized against cell counts, or expressed as a percentage of the baseline oxygen consumption.

K) In Vivo Orthotopic Xenograft Tumorigenesis Assay

NSG mice were purchased from The Jackson Laboratory and experiments were performed at the Istanbul Medipol University. All mice were maintained in a specific pathogen-free facility and all animal experiments were performed in accordance with protocols approved by the Institutional Animal Care and Use Committees of the Istanbul Medipol University. A549 WT and A549 HK1b$^{-/-}$ cells were orthotopically injected into immunodeficient NSG male mice to induce orthotopic NSCLC tumor model. Relative tumor volume was measured in 8 weeks after implantation and, is calculated as follows: (length×width×height)×π/6. End points were reached, and mice were killed once the tumor size measured 2 cm.

L) Immunofluorescence and Microscopy

Cells were seeded on 8-well chamber culture slides (Lab-Tek II, Thermo Fisher Scientific). After appropriate treatment or transfection, the cells were fixed with 4% paraformaldehyde (Wako) for 20 minutes at room temperature and permeabilized with 0.5% Triton-X100 in PBS buffer for 15 minutes. The cells were incubated overnight at 4 C with primary antibodies for HK1, p53 diluted in PBS with 3% BSA. After three 10-minute washes in PBS, the cells were incubated for 60 minutes at room temperature with fluorochrome-conjugated secondary antibodies. Culture slides were washed three times for 10 minutes in PBS. For imaging, cells were stored in Vectashield hard set mounting medium with DAPI (H1500, Vector Laboratories). Cell imaging was accomplished with a a FV-1000 confocal microscope (Olympus).

M) Structure Preparation

We used crystal structures of HK1b (PDB ID: 1QHA) and HK2 (PDB ID: 2NZT), whereas HK1c was modeled using SWISS-Homology-Modeling-Software. Unresolved parts of the crystal structures were modeled with Swiss-Modeller, and loop regions were refined with ModLoop. The protonation states of residues were determined using PROPKA. Glucose was used in beta conformation. ATP and Mg2+ were translated to each system from crystal structure of Glucokinase (PDB ID: 3FGU).

N) Molecular Dynamics Simulations

MD simulations were performed with GROMACS 5.1.4 employing CHARMM 36 force-field. Systems were subjected minimized using a conjugate gradient algorithm. All systems were energy relaxed with 1000 steps of steepest-descent. The systems were equilibrated using NVT ensemble with Berendsen-algorithm. The final structures were run in NPT ensemble at 1 atm and 310 K. MD simulations were run for 300-ns. All coordinates were saved at 2-ps intervals for analysis. Long-range electrostatic forces were handled using PME, and Van der Waals forces treated with a 0.9-nm-cut-off. Water molecules were modelled with TIP3P model.

O) Statistical Analysis

Unless otherwise stated, data are expressed as mean±SEM. GraphPad Prism 8 software was used for graphing and statistical analysis. After calculating normality by Shapiro-Wilk test, Student t or Mann-Whitney test were used to compare two samples. For multiple group comparisons, One-way ANOVA analysis and followed by Tukey's multiple comparison tests were used. Statistical parameters including exact value of n, statistical test and significance are reported in the figures and figure legends. Values of $p<0.05$ were considered statistically significant.

2) Results

Figure 5:
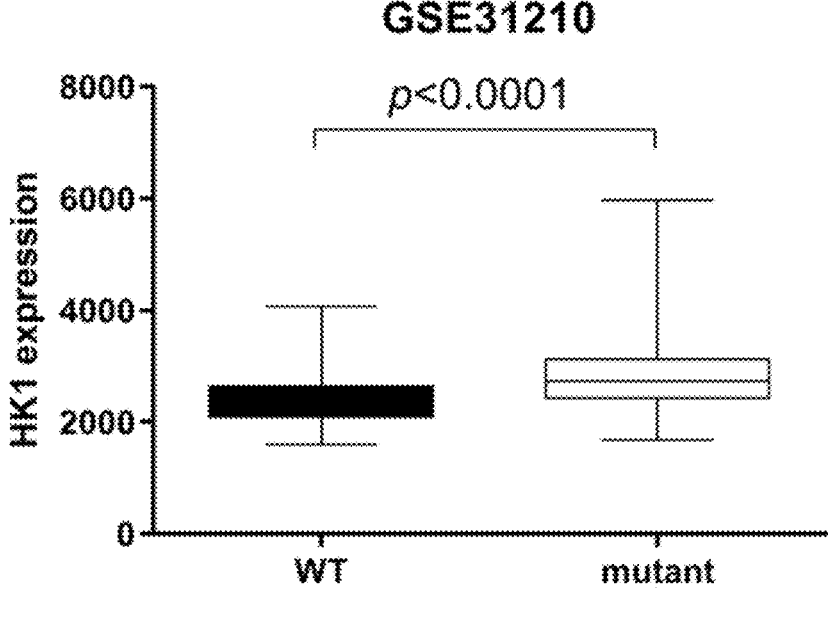
Figure 6:
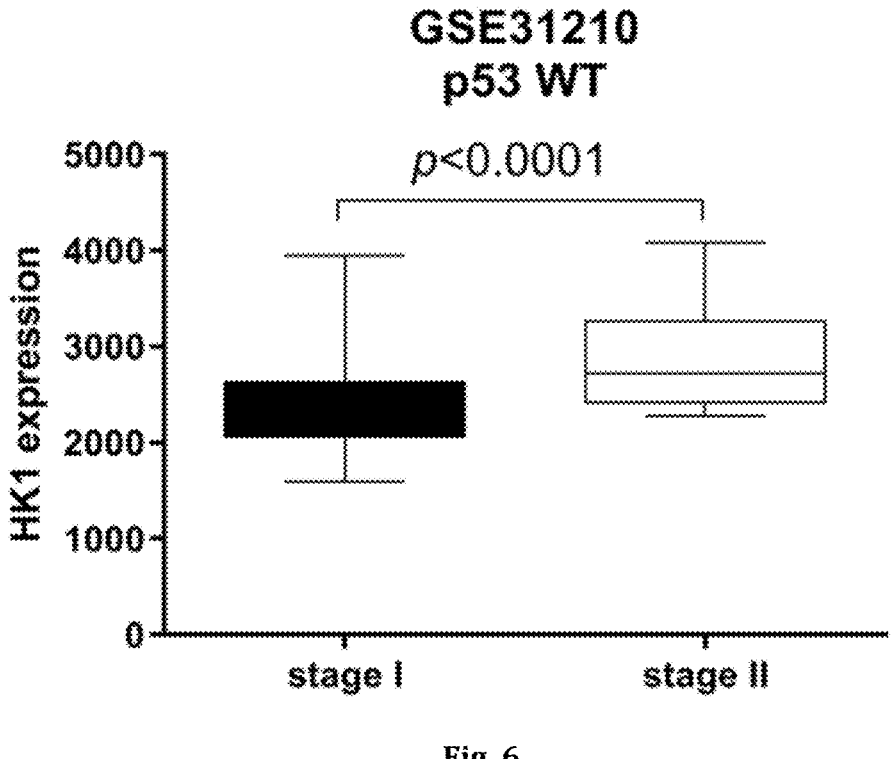
Figure 7:
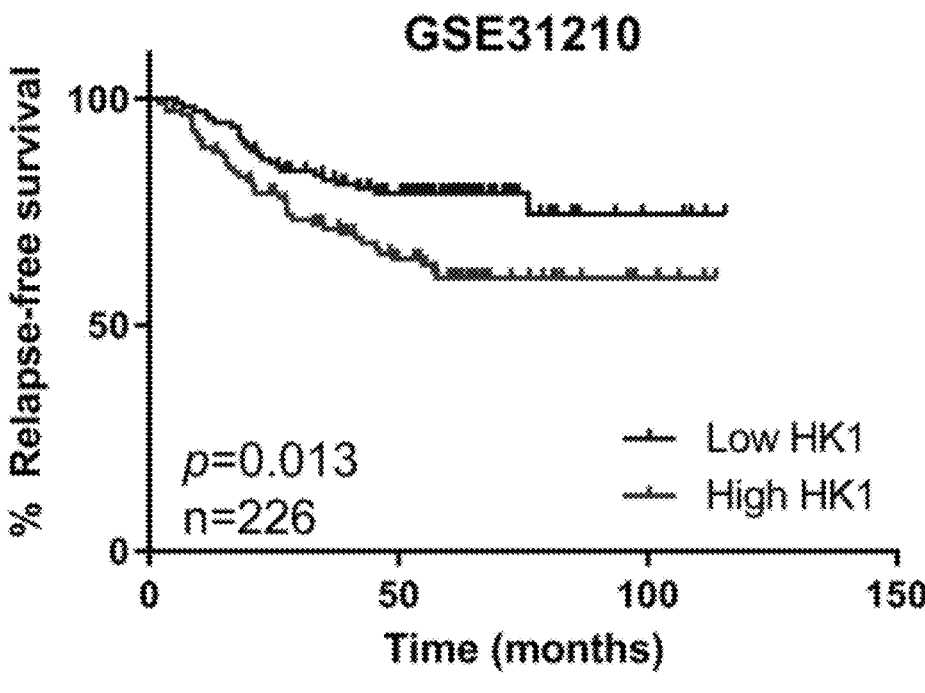

A) HK1 Expression is Upregulated in Human NSCLs and is Associated with a Poor Clinical Outcomes in Patients To validate specific upregulation of HK1 in human NSCLC, we analyzed human NSCLC tumor tissues and adjacent non-tumor lung tissues for the expression of HK1 along with HK2 and p53 for comparison. We found that in a small cohort of patients, HK1, HK2 and p53 were upregulated in NSCLC tumor tissues as compared to normal lung tissue from the same patients by immunoblotting (FIGS. 1 and 2). However, quantification of band intensities of HK1 and HK2 revealed that human NSCLC tumors have significantly higher HK1 expression than HK2 (FIG. 3), suggesting that HK1 is more ubiquitously overexpressed in NSCLC than HK2 despite the small sample size. We further evaluated of the in situ expression of HK1 in NSCLC cells by immunohistochemistry. All the noncancerous epithelium showed weak staining of HK1, while tumor cells showed moderate to strong staining of HK1 (FIG. 4). To extend the data, we performed the comparison between NSCLC and normal samples in TCGA RNA-Seq data. Patients were separated as p53 WT and mutant based on the expression of the p53 gene signature as described previously. The analysis revealed that patients with mutant p53 express higher levels of HK1 (FIG. 5). Moreover, stage II patients have higher HK1 expression only in p53 WT group (FIG. 6), suggesting that HK1 expression correlates with tumor grade and the disease stage in NSCLC. Lastly, survival analysis showed that higher expression of HK1 was associated with decreased relapse-free survival (P=0.01; FIG. 7), suggesting that higher HK1 expression is associated with disease progression.

Figure 8:
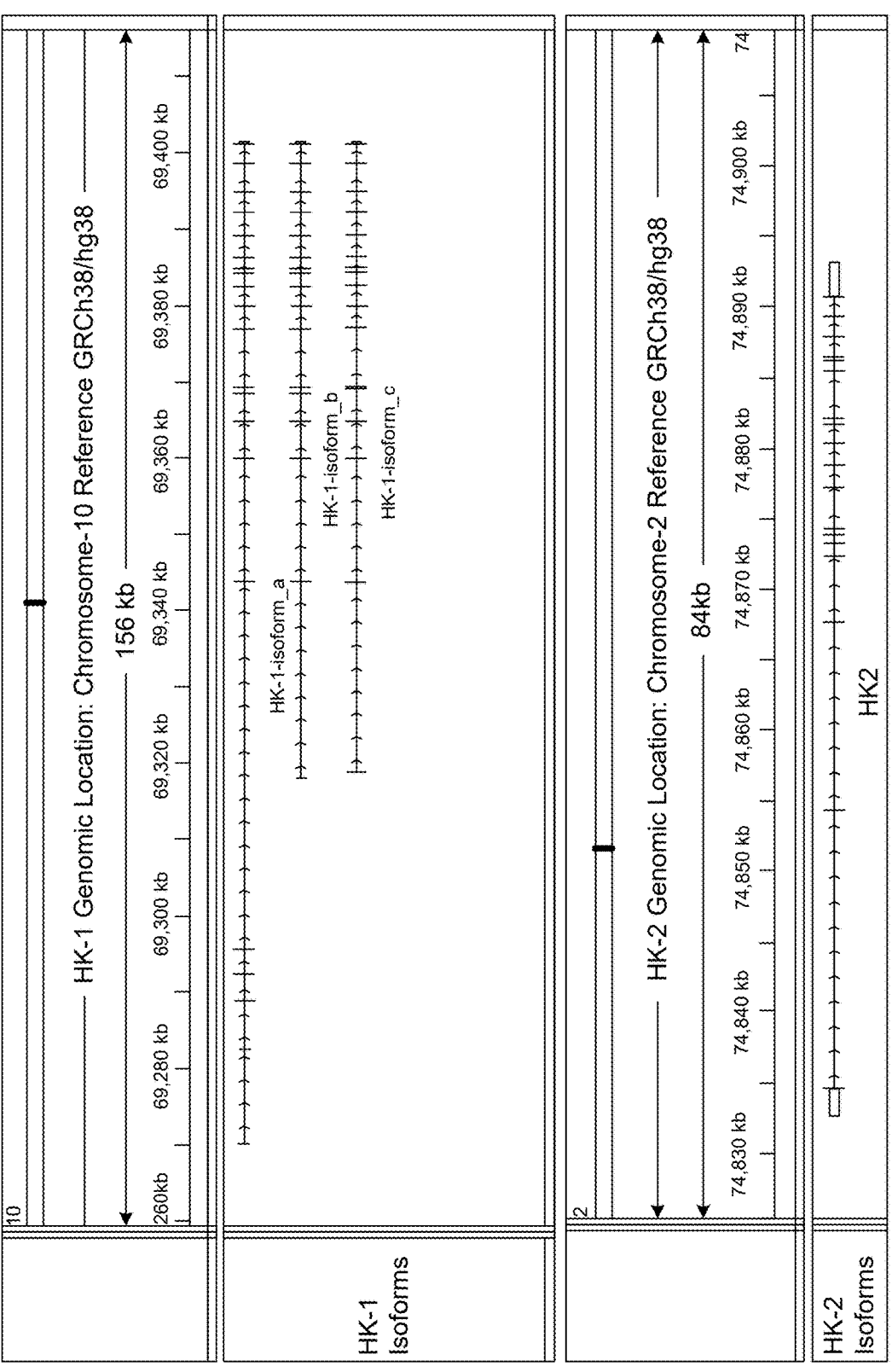
FIGS. 8-10 shows the RefSeq HK1 gene transcript variants and HK2 gene transcript and Structural differences of HK1b isoform molecular dynamics simulations.
Figure 9:
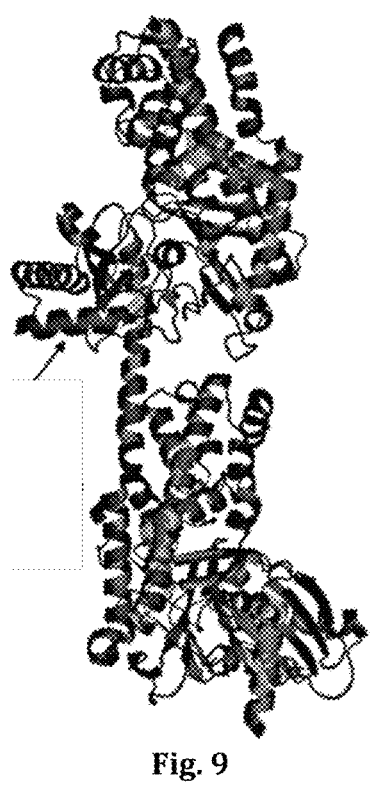

B) Human NSCLC Cells Express Mainly Only One of the HK1 Isoforms-Hexokinase1b (HK1b) as a Poor Prognostic Factor The HK1 gene spans approximately 131 kb and consists of 25 exons. According to RefSeq gene annotations, alternative splicing of HK1 gene at its 5' end produces different transcripts in different cell types. The testis-specific exons are located at approximately 15 kb upstream of the erythroid-specific exon R. The first 5 exons of the HK-I gene encode the testis-specific sequences. The 6th exon is the erythroid-specific exon R [10]. When we exclude these tissue specific transcripts we have 3 remaining transcripts that we are focused on: HK1a, HK1b and HK1c. On the other hand the HK2 gene has one transcript in the RefSeq gene annotations (FIG. 8). Although, there are a few studies on the testis specific transcripts [11], the differential expression of these three isoforms of the HK1 gene in different tissues (including the cancer tissues) and their functionality have not been shown. When we analyze the HK1 transcripts, it is possible to differentiate them using the differentially used exons. HK1a transcript contains different exons at the 5' end and therefore it is possible to differentiate this transcript Differentiating HK1b and HK1c isoforms is more difficult due to the highly shared exons between them. Both Hk1b and HK1a isoforms possess one extra exon, exon 8, which is missing in the HK1c isoform. Using these exon-exon junctions around exon 8, we were able to design specific genomic probes to differentiate HK1b and HK1c isoforms. Therefore, targeting these exons will allow us to quantify the expression of these transcripts in different tissues.

Figure 11:
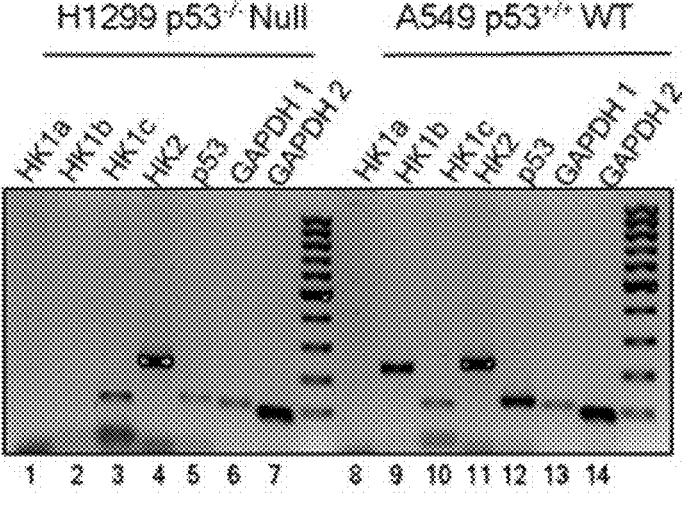
FIGS. 11-14 shows HK1b isoform upregulation in NSCLC patients.
Figure 12:
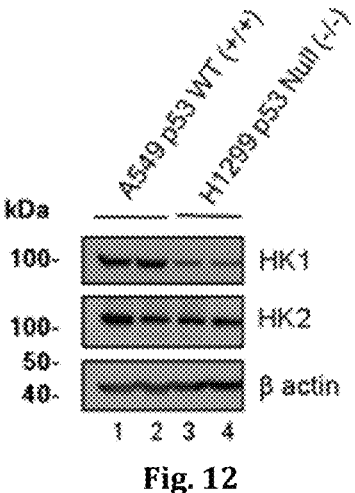

To identify new, HK1 isoform specific metabolic target for the treatment of NSCLC, we first analyzed HK1 isoforms (HK1a, HK1b, and HK1c) along with HK2 and p53 in NSCLC adenocarcinoma cell lines (p53 WT-A549 and p53 null-H1299). Semi-q-PCR data of both A549 and H1299 cells showed that HK1a isoform is not specific to NSCLC because of its absent expression. HK1b isoform predominantly expressed in p53 WT A549 cells, but not in p53−/−H1299 cells. However, we observed no difference in the levels of HK1c and HK2 expressions between A549 and H1299 cells (FIG. 11). Since there is no available isoform specific antibody to detect HK1 isoforms, we used HK1 antibody to detect the level of its expression in both A549 and H1299 cells. Therefore, we further validated the PCR results by immunoblot analysis that HK1 protein expression was higher in A549 cells than H1299 cells and HK2 expression levels were not changed on both cells (FIG. 12), indicating that HK1b expression was specific to A549 cells.

Figure 13:
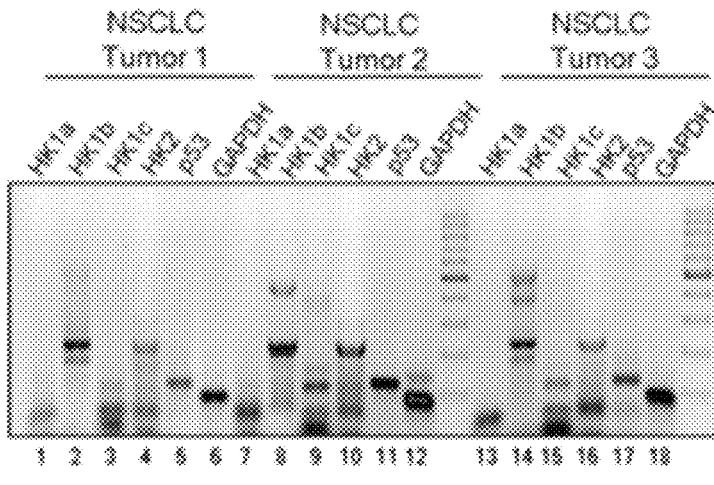
Figure 14:
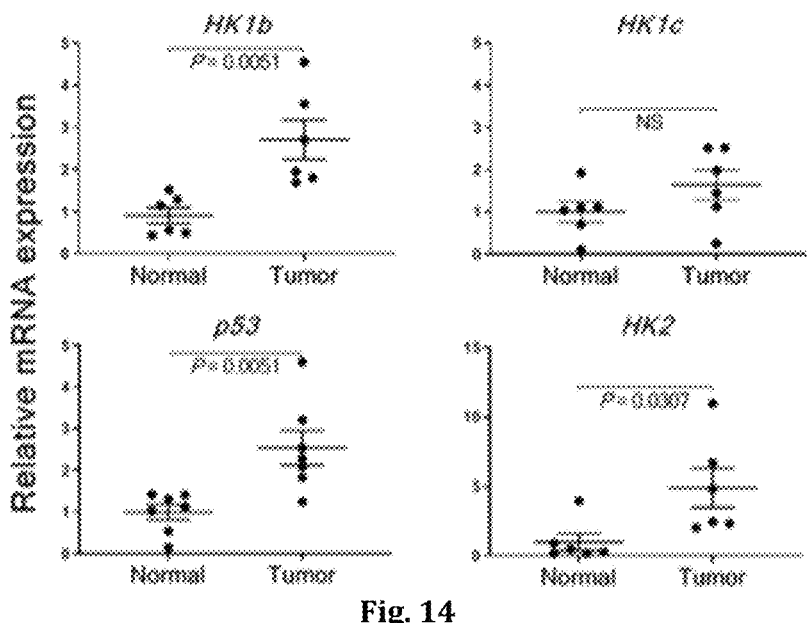
Figure 15:
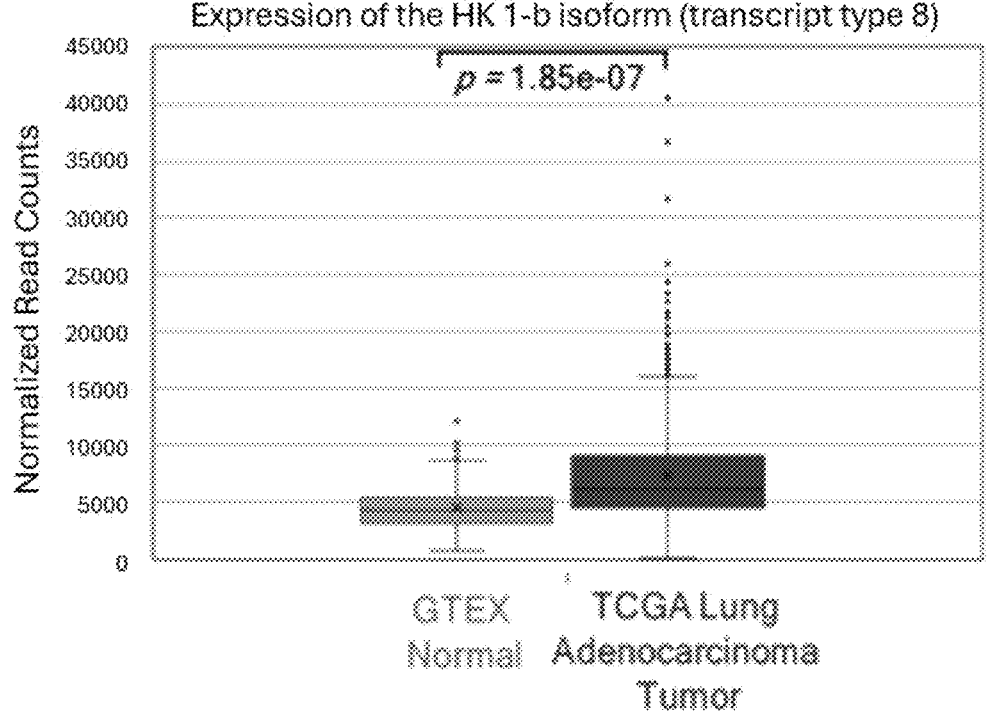
FIGS. 15-17 shows that increased expression of the HK1b isoform is associated with worse prognosis from TCGA NSCLC patient data.
Figure 16:
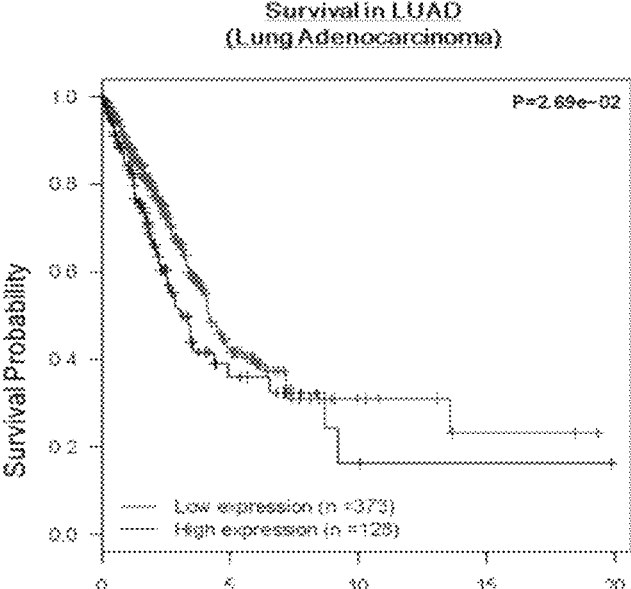
Figure 17:
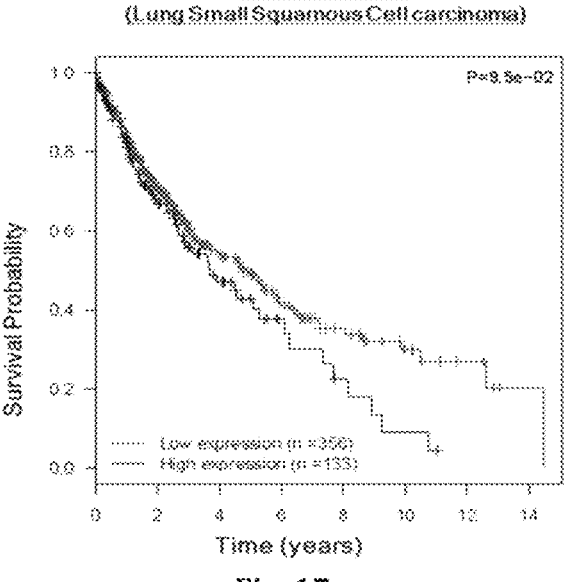
Figure 18:
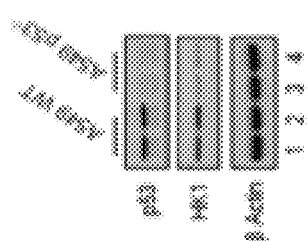
FIG. 18 depicts qRT-PCR for level of HK1 b, c, HK2, and p53 in A549 p53−/− cells. Error bars indicate mean±SEM, (n=3) and immunoblot analysis of p53 KO in A549 cells.
Figure 18:
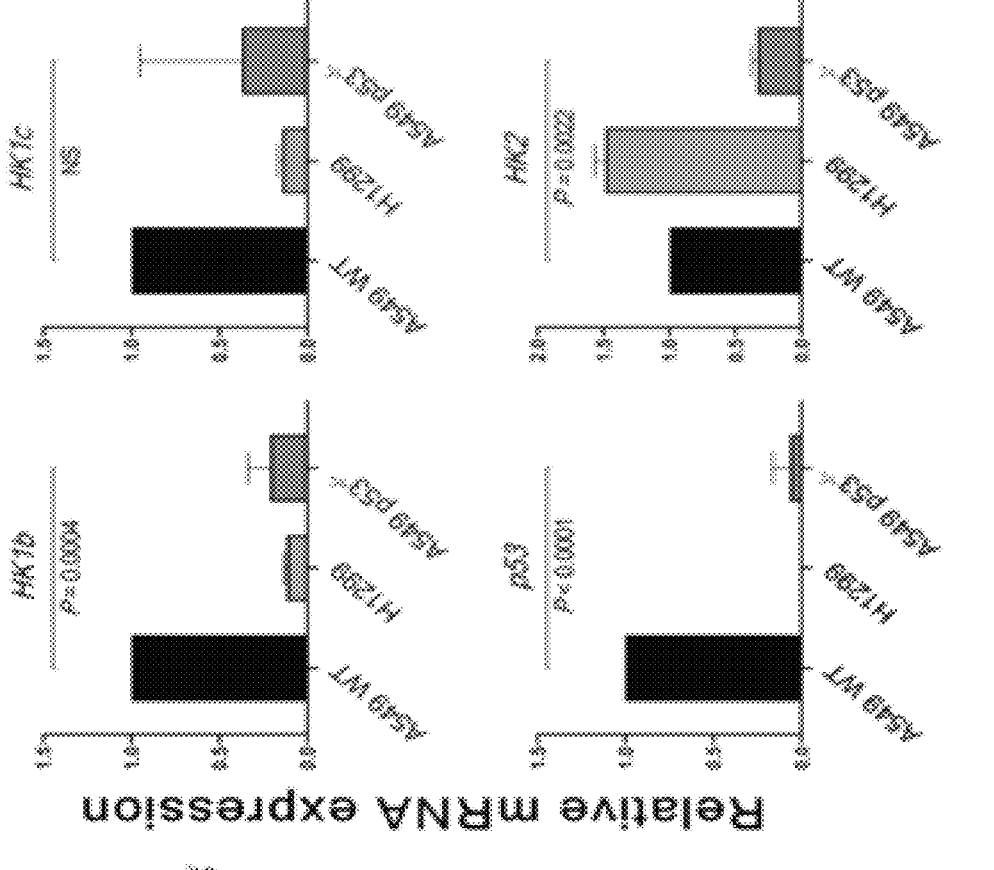
Figure 19:
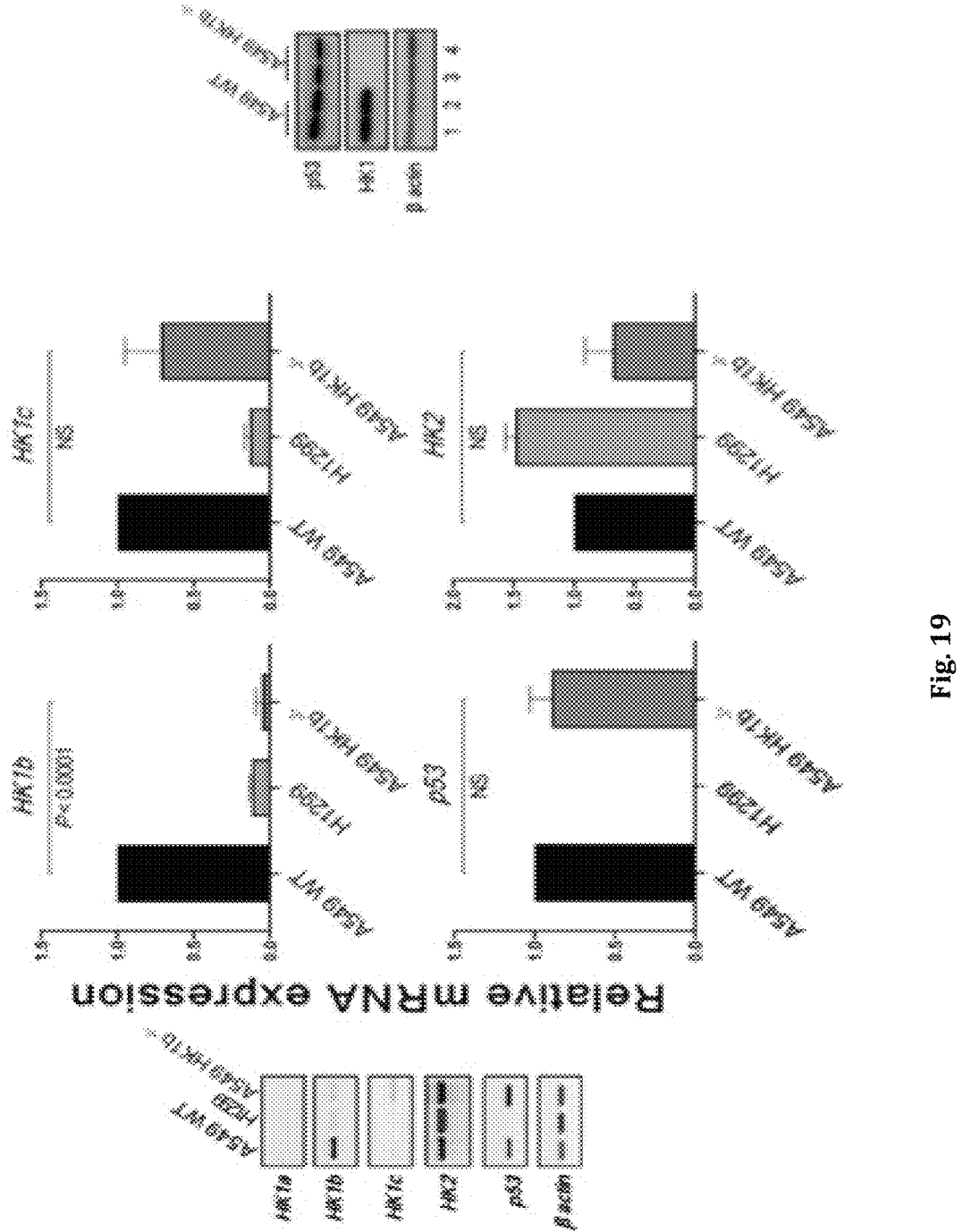
FIG. 19 depicts qRT-PCR for level of HK1 b, c, HK2, and p53 in A549. Error bars indicate mean±SEM, (n=3) and immunoblot analysis of HK1b KO in A549 cells.
Figure 20:
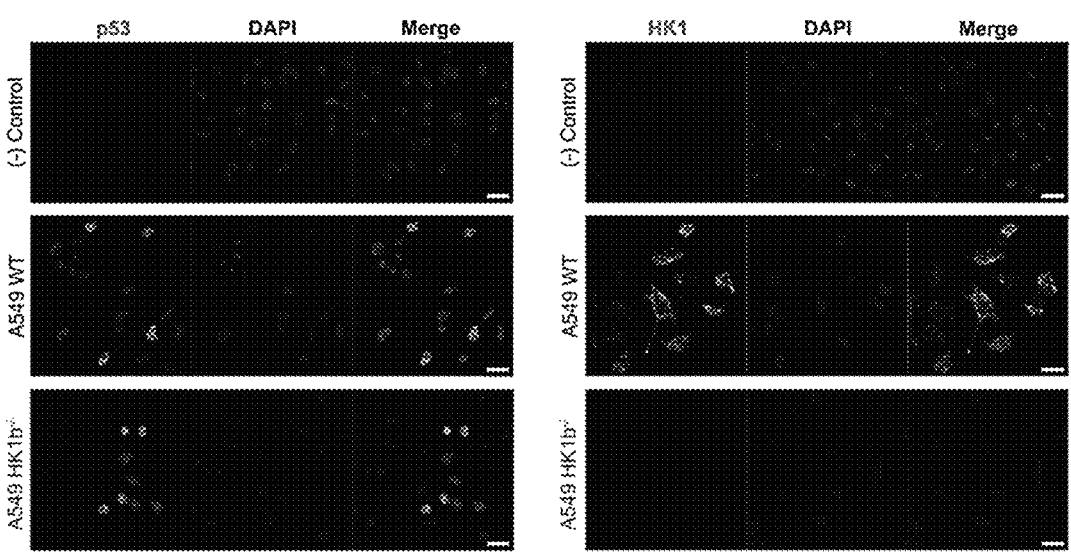
FIG. 20 depicts immunofluorescence and Immunoblot analyses of A549 WT and A549 HK1b−/− cells, using HK1 antibody showed the total absence of endogenous HK1 protein and no change in level of endogenous p53 protein.

To evaluate the clinical relevance of HK1b upregulation in human NSCL cancer, we performed semi-q-PCR and qRT-PCR analyses on tumors and adjacent non-tumor samples from NSCLC patients. In particular, HK1b was more significantly (p=0.005) upregulated than HK2 transcript (p=0.03) in the NSCLC tumor to those compared to normal adjacent tissue (p=0.005). (FIG. 13 and FIG. 14). Hk1c isoform expression was not significant, supporting the idea that Hk1b was uniquely upregulated in comparison to HK1c isoform and HK2. Interestingly, p53 gene expression also increased (p=0.005) similar to HK1b. Similar to A549 NSCLC cells, NSCLC patient tumor cells showed no expression of HK1a isoform (FIG. 13 and FIG. 14). In order to further validate the increased expression of the HK1b isoforms between the NSCL adenocarcinoma and the normal lung tissues, we merged the most extensive public databases TCGA (The Cancer Genome Atlas) Project and the GTEx (Genotype-Tissue Expression) Project. TCGA Lung Adenocarcinoma project contains 426 RNA sequencing of lung tumor tissues. These tumor samples are matched with 602 normal lung tissues from the GTEx Project. For each database the supplied expected transcript read counts that are generated using the RSEM software package is used for the comparison. The read counts are normalized using the DESeq2 variance stabilized normalization method. Consistent with RT-PCR analyses, the comparison of the expression of the HK1b isoform (transcript variant-8) between normal and TCGA Lung adenocarcinoma samples (RefSeq id NM_001322366) showed a significant upregulation of HK1b in NSCLC tumor tissues compared with those in normal lung tissues (p=1.85e-07) (FIG. 154.2.3.A). Altogether, these data reveal that elevated HK1b expression is specific to NSCLC across a wide selection of lung cancer patients when compared to normal lung tissues. Moreover, higher expression of the HK1b isoform is associated with decreased survival probability for both adenocarcinoma (FIG. 16) and squamous cell carcinoma (FIG. 17) types of NSCLC, albeit the latter is not significant (p=2.69e-02, p=9.5e-02, respectively). Collectively, our data provide compelling evidence for the specificity of HK1b isoform in NSCLC which may be utilized as an attractive metabolic target.

C) the Effect of HK1b Deficiency on Metabolism, Proliferation, and Tumorigenesis in NSCLC Cells.

Figure 10:
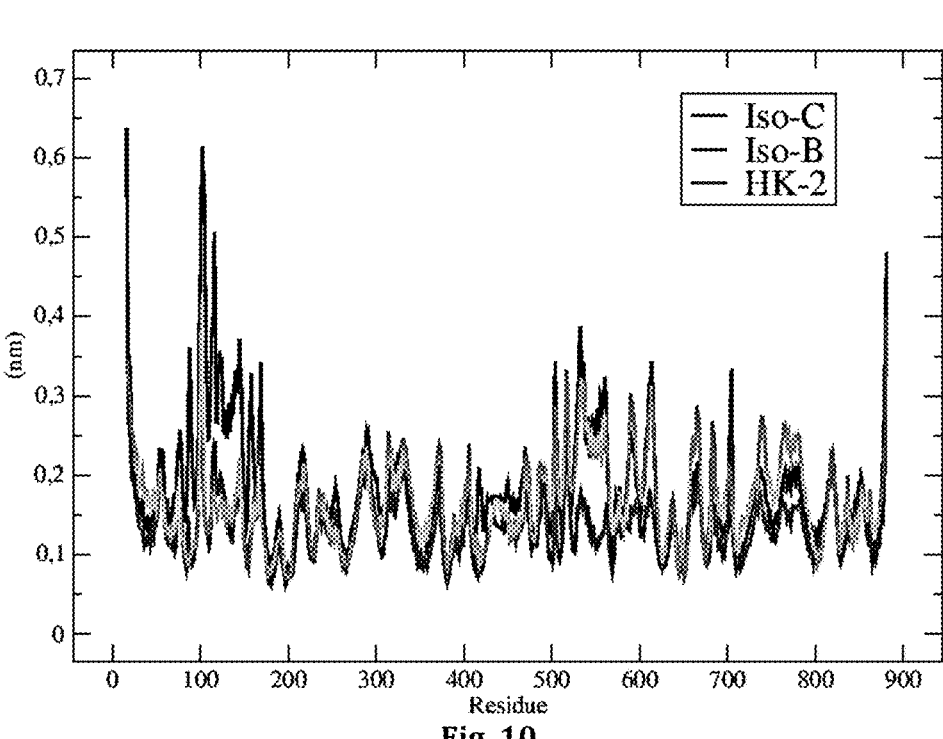

It is known that the N-terminal of HK1 and HK2 is responsible for providing stability to overall enzyme and for binding to the outer mitochondrial membrane. Although HK1a, b, c and HK2 have structural similarities, differences in N-terminal sequence make them unique, and this reflects significantly to change in metabolism hence tumorigenesis. Herein, our finding of structural differences suggesting that HK1b isoform contained unique sequences that might mediate the stability of N-domain, which is shown by root-mean square fluctuation analysis, (FIG. 10), thus increasing the strength of the interaction between mitochondria and HK1 b.

Figure 21:
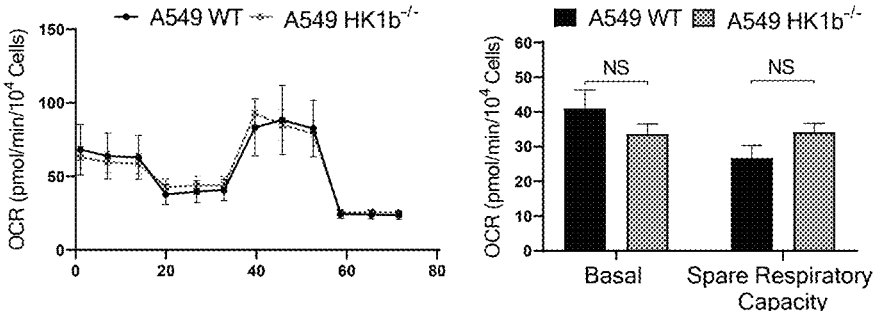
FIG. 21-23 demonstrates that NSCLC cells dependent on glycolysis and HK1b is crucial for glycolytic activity in NSCLC cells using the Seahorse metabolic analyzer.
Figure 22:
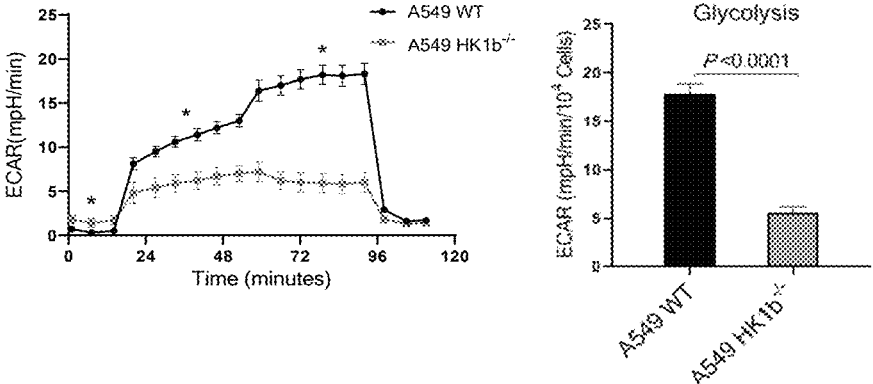

All together these data suggest that HK1b might have major role in glycolysis hence NSCLC tumorigenesis. To understand the mechanisms and HK1b isoform functional role in proliferation, survival, and tumorigenesis, we analyzed the metabolic consequences of HK1b isoform deficiency. Changes in glycolysis and respiration were measured after deletion of HK1b using the Seahorse metabolic analyzer. Analysis of the mitochondrial respiration rate following HK1b knockout (KO) showed not significant change in oxygen consumption rate (OCR) and respiration (FIG. 21), suggesting that HK1b ablation induce maintenance of the mitochondria-driven OXPHOS. However, measuring extracellular acidification rate (ECAR) using the XF glycolysis stress test and the XF glycolytic rate assay showed significant reductions in glycolytic activity in A549 cells upon HK1b isoform loss (A549 HK1b$^{-/-}$) compared to control cells (A549 WT) (p=0.0001 and p=0.002, respectively)) (FIG. 22). Moreover, we next determined the metabolic fuel dependencies and capacities of A549 WT and A549 HK1b$^{-/-}$ cells. We found that A549 HK1b$^{-/-}$ cells had significant lower glucose dependencies (p=0.006) and no significant change on either glucose capacities or on both glutamine dependencies and capacities compared to A549 WT cells. These suggest that A549 prefer glucose over glutamine and deletion of HK1b functions as a glycolytic regulator and has an extensive role in glucose metabolism. Interestingly, HK1b deletion significantly increased the fatty acid dependencies (p<0.0001) and the fatty acid capacities (p=0.03). Indeed, cancer cells become increasingly dependent on mitochondrial fatty acid oxidation in nutrient-depleted conditions in previous studies.

Figure 23:
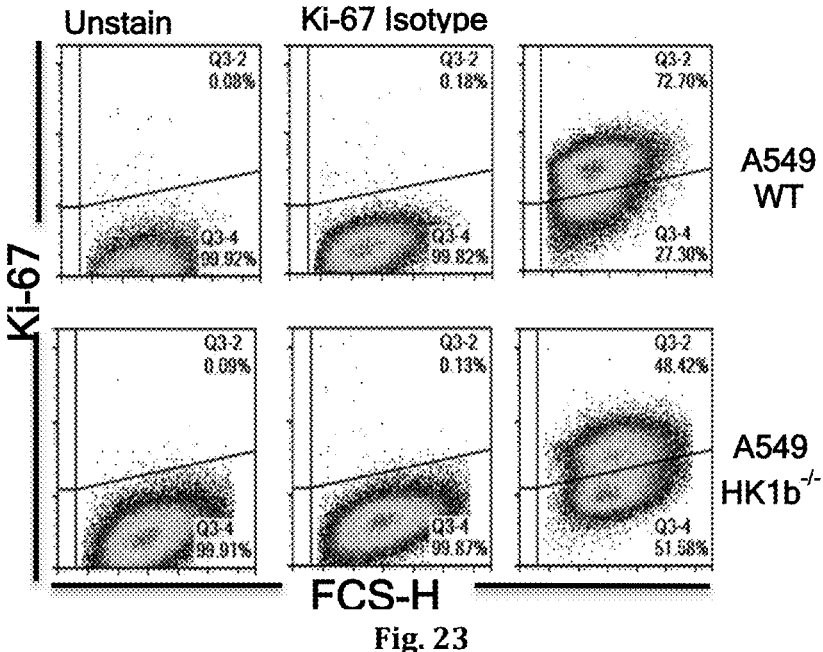
Figure 24:
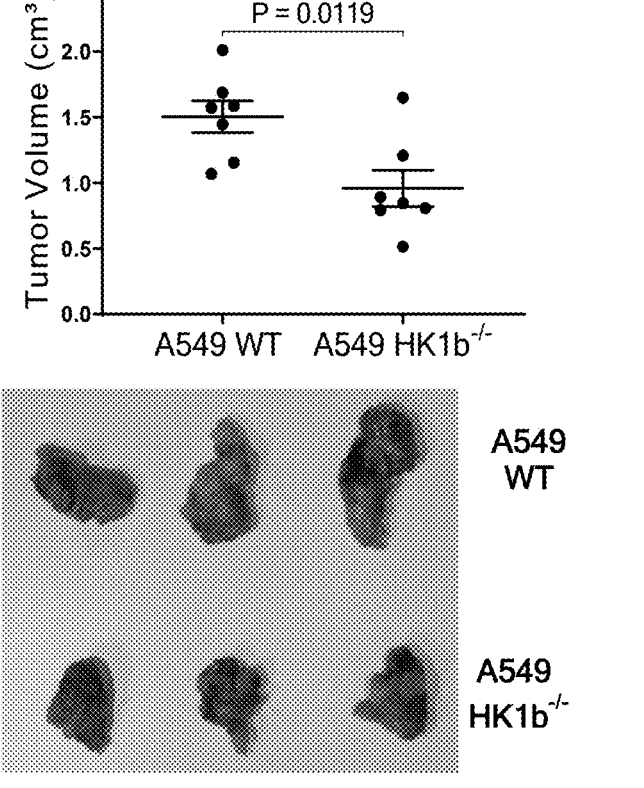
FIGS. 24 and 25 depicts the effect of HK1b knockout on tumorigenicity of A549 cells.
Figure 25:
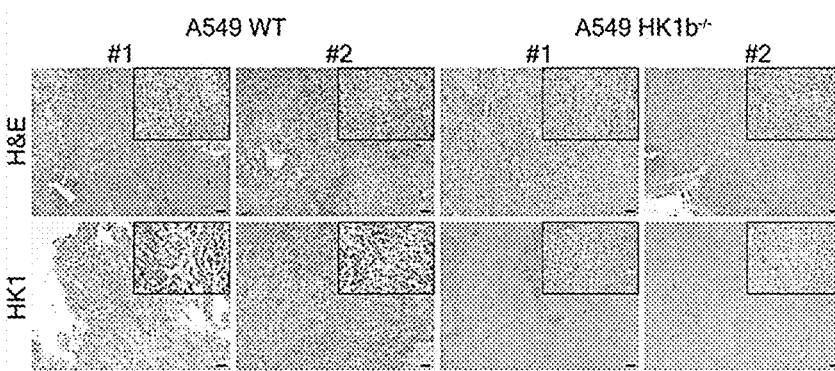

In order to evaluate the effect of reduced glycolysis on proliferation in vitro, flow cytometry analyses of Ki67, a marker for proliferation, was performed and A549 HK1b$^{-/-}$ cells showed an approximately 35% decrease of Ki-67 level (FIG. 23). Importantly, to test potential tumorigenic role of HK1b in vivo, A549 WT and A549 HK1b$^{-/-}$ cells were orthotopically injected into immunodeficient NSG male mice to induce orthotopic NSCLC tumor model. Relative tumor volume was measured in 8 weeks after implantation. Tumor size was significantly reduced by 35% in mice bearing A549 HK1b$^{-/-}$ cells (p=0.01) (FIG. 24). Histopathology characterization of xenografts from A549 WT or A549 HK1b$^{-/-}$ cells showed both are NSCLC lung adenocarcinoma. Staining of tumor tissue with HK1 confirmed that no HK1 expression observed in tumor from bearing A549 HK1b$^{-/-}$ mice in comparison to tumors from bearing A549 WT mice (FIG. 24). Immunohistochemical analysis of Ki67 in tumor tissues showed that tumors with HK1b$^{-/-}$ had significantly lower Ki67 stainings compared to those with WT (p=0.001) (FIG. 25), indicating that HK1b KO cells have less proliferation ability. All these data show that inhibition of HK1b reduces cell proliferation and tumor growth by mitigating glycolysis in NSCLC.

Figure 26:
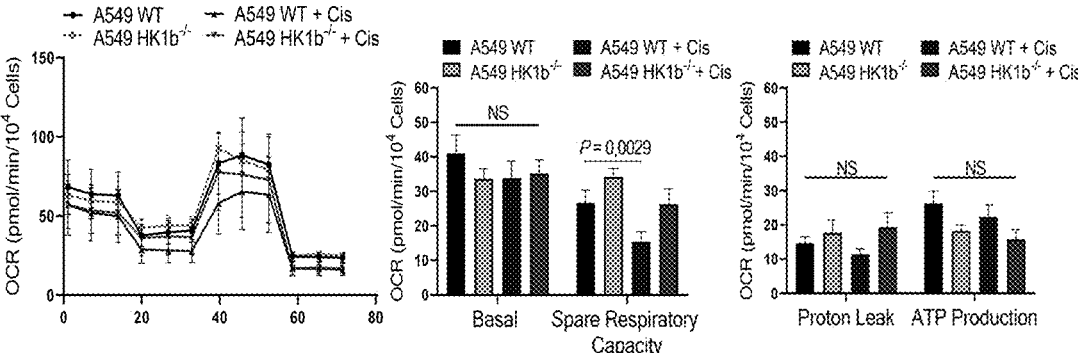
FIG. 26 depicts the analyses of the mitochondrial respiration rate of A549 WT and A549 HK1b$^{-/-}$ cells upon cisplatin treatment Showing that no significant change of basal respiration rate
Figure 27:
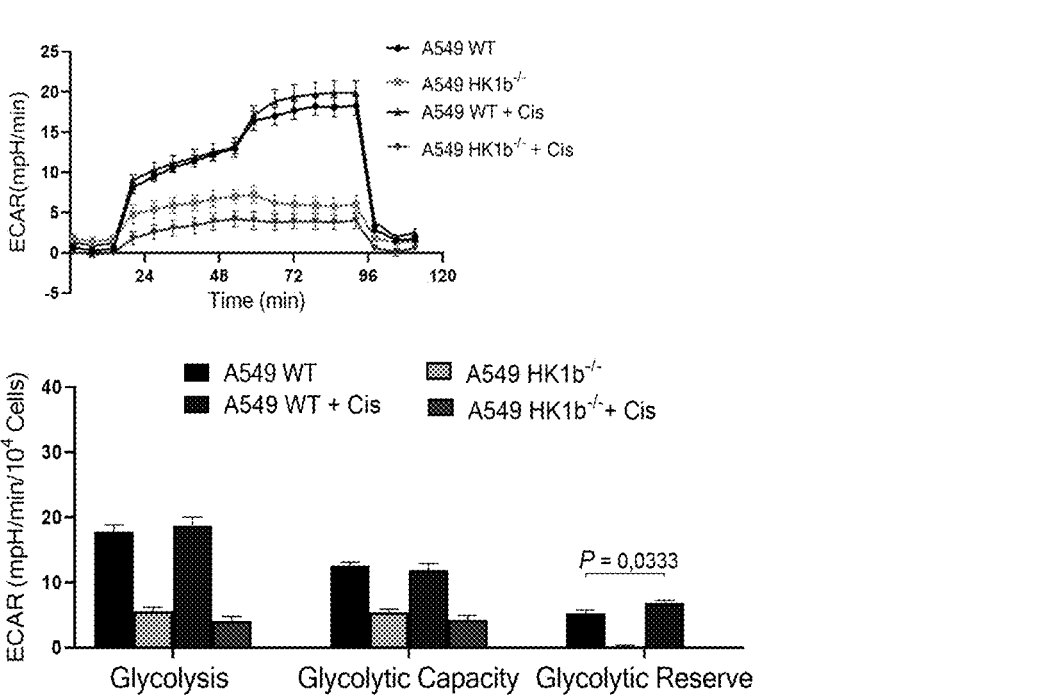
FIG. 27 depicts the the results of measuring extracellular acidification rate (ECAR) of A549 WT and A549 HK1b$^{-/-}$ cells upon cisplatin treatment using the XF glycolysis stress test showing that basal glycolysis and glycolytic capacity further reduced ablait not significant, and total absence of glycolytic reserve on cisplatin treated A549 HK1b$^{-/-}$ cells. Results are the mean+/–SD of 3 independent experiments. P-values were calculated using Student's t-test (*, P<0.001)

D) the Effect of HK1b KO and Cisplatin Treatment on Metabolism, Drug Effect, and Survival Pathway in NSCLC Cells The treatment options for NSCLC are based mainly on several factors but in general chemotherapy often is one of the first line therapies for NSCLC patients. Cisplatin is slightly more effective platinum widely used in the treatment of NSCLC. However, it has been reported that cisplatin has been associated with more side effects. Moreover, inhibitors targeting metabolic changes have been developed as a potential therapeutics and several are now in early-phase clinical trials However, the efforts have been made so far not successful because of adverse side effect of drugs. Therefore, there is a clinically unmet need for precise and effective metabolic therapeutic target in cancer cells to improve survival and reduce disease-related adverse events in NSCLC patients. We first hypothesized that HK1b elimination and cisplatin could synergize to decrease glycolysis further that could potentially be therapeutic for NSCLC since the loss of HK1b led to a reduction in glycolysis. We observed further reduction of basal glycolysis and glycolytic capacity even though not significant, and total absence of glycolytic reserve on cisplatin treated A549 HK1b$^{-/-}$ cells (FIG. 21). No significant change of basal respiration rate was observed in between both cisplatin treated A549 WT and A549 HK1b$^{-/-}$ cells. However, only spare respiratory capacity was diminished in cisplatin treated A549 WT cells (p=0.02) (FIG. 26-27).

Figure 28:
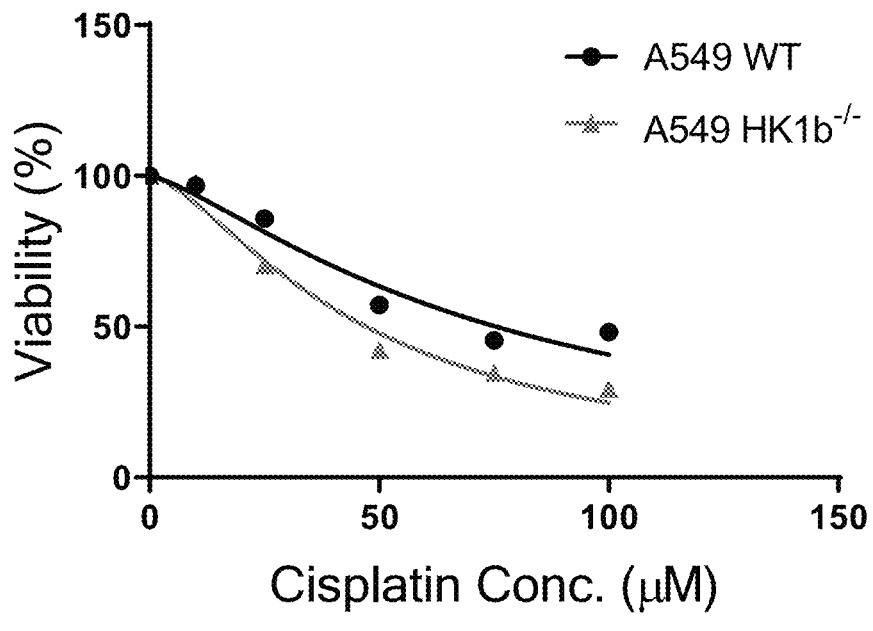
FIG. 28** depicts the results of cell viability assay and A549 HK1b$^{-/-}$ cells showed significantly lower IC50 value (47 μM) than the A549 WT control group (75 μM).
Figure 29:
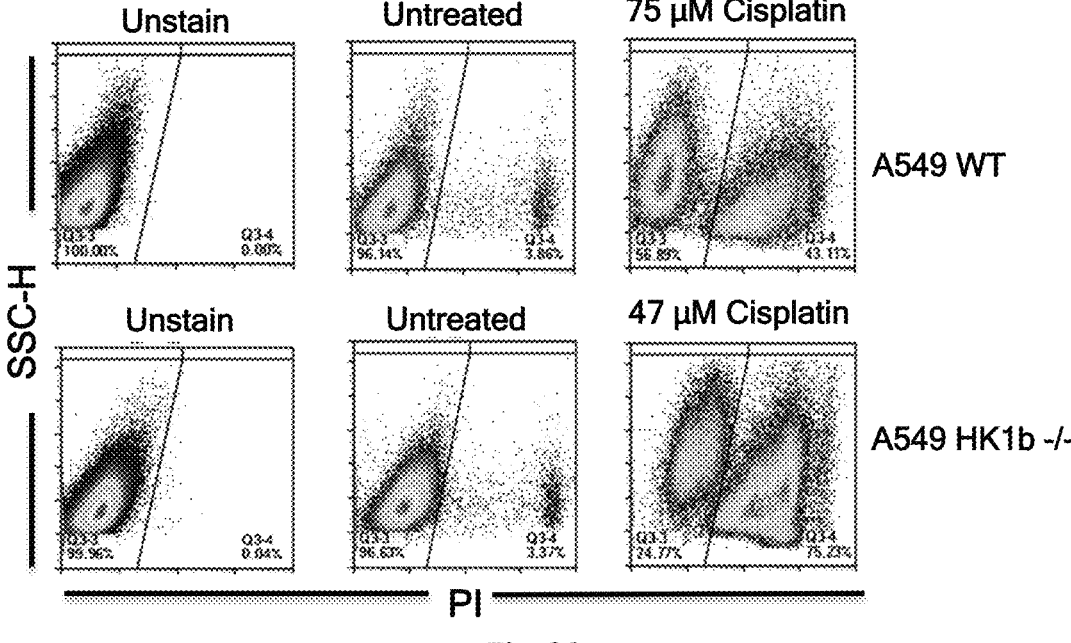
FIG. 29 depicts the flow cytometric quantification analyses of cell death measured by propidium iodide (PI) staining and showed that synergetic effect of Hk1b deletion and cisplatin significantly enhance cell death in A549 HK1b$^{-/-}$.
Figure 30:
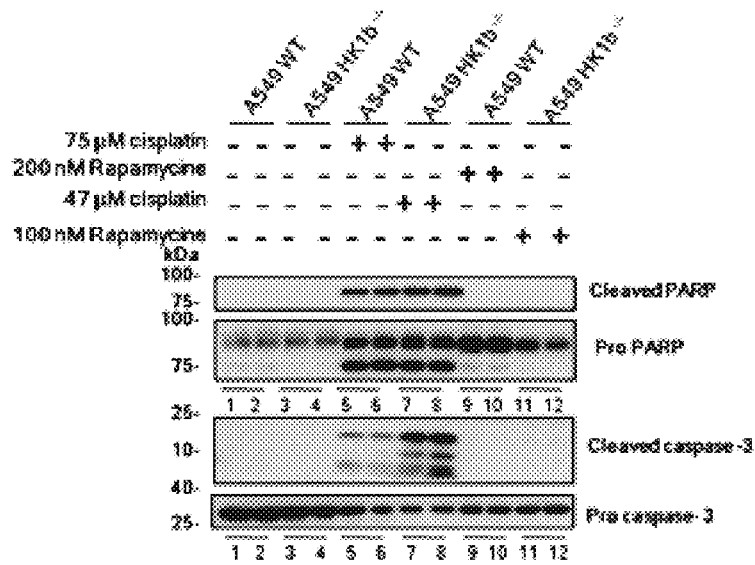
FIG. 30 depicts the immunoblot analyses of apoptotic pathway using also rapamycine as a control treatment and showed that only cisplatin treatment induces cleavage of PARP and caspase 3 but induction of cleavage was significantly higher in A549 HK1b$^{-/-}$ cells.
Figure 31:
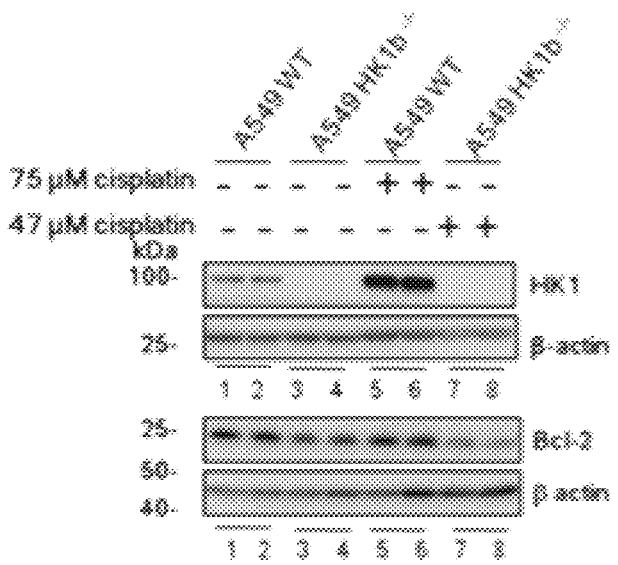
FIG. 31 depicts immunoblot analysis of HK1 and Bcl-2. Anti-beta-actin is used as a loading control.

We next investigated whether the HK1b deletion could sensitize NSCLC cells to cisplatin treatment and evaluated the drug effect of cisplatin with or without HK1b ablation. Cell viability assay was performed and A549 HK1b$^{-/-}$ cells showed significantly lower IC50 value (47 μM) than the A549 WT control group (75 μM) (FIG. 28). Flow cytometric quantification of cell death measured by propidium iodide (PI) staining. Synergetic effect of Hk1b deletion and cisplatin significantly enhance cell death in A549 HK1b$^{-/-}$ cells (FIG. 29). Furthermore, we found that only cisplatin treatment induces cleavage of PARP and caspase 3 but induction of cleavage was significantly higher in A549 HK1b$^{-/-}$ cells (FIG. 30). We used rapamycin treatment as a control and we found that cisplatin but not rapamycin treatment induce apoptosis (FIG. 30) and HK1b elimination with cisplatin promoted greater cisplatin-induced cellular apoptosis. Interestingly, HK1b deletion slightly induces down-regulation of Bcl-2 expression in untreated A549 HK1b$^{-/-}$ cells and down-regulation of Bcl-2 expression was significant with the cisplatin treatment (FIG. 31). Indeed, HK1 or HK2 plays a clear role in protecting against mitochondrial regulated apoptosis through direct interaction with mitochondria. Surprisingly, HK1, but not HK2, expression was significantly upregulated in cisplatin treated A549 WT cells (FIG. 31), indicating that HK1 (mainly HK1b isoform) is specific to NSCLC. We also observed that HK2 expression was reduced in cisplatin treated A549 HK1b$^{-/-}$ cells (FIG. 31). These results suggest that loss of HK1b sensitizes NSCLC cells to cisplatin to induce apoptosis in NSCLC cells.

Figure 32:
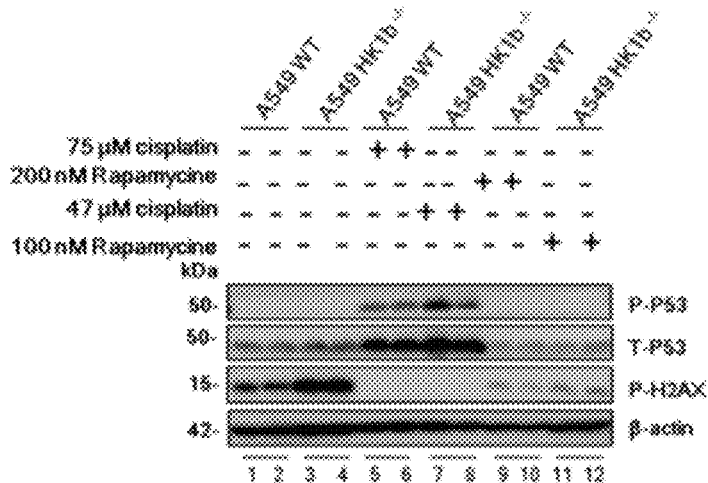
FIG. 32 shows the synergetic effect of HK1b ablation and cisplatin increases p53-mediated apoptotic cell death. Immunoblot analysis of cells treated with cisplatin (75 μM and 47 μM, respectively) or rapamycin (100 μM and 47 μM, respectively) and immunoblot analysis of p53 and H2AX B. Also, representative transmission electron microscopy (TEM) micrographs displaying characteristics of apoptosis is given; images are representative of two independent experiments; scale bar, 1 μm (left) and 400 nm (right).
Figure 32:
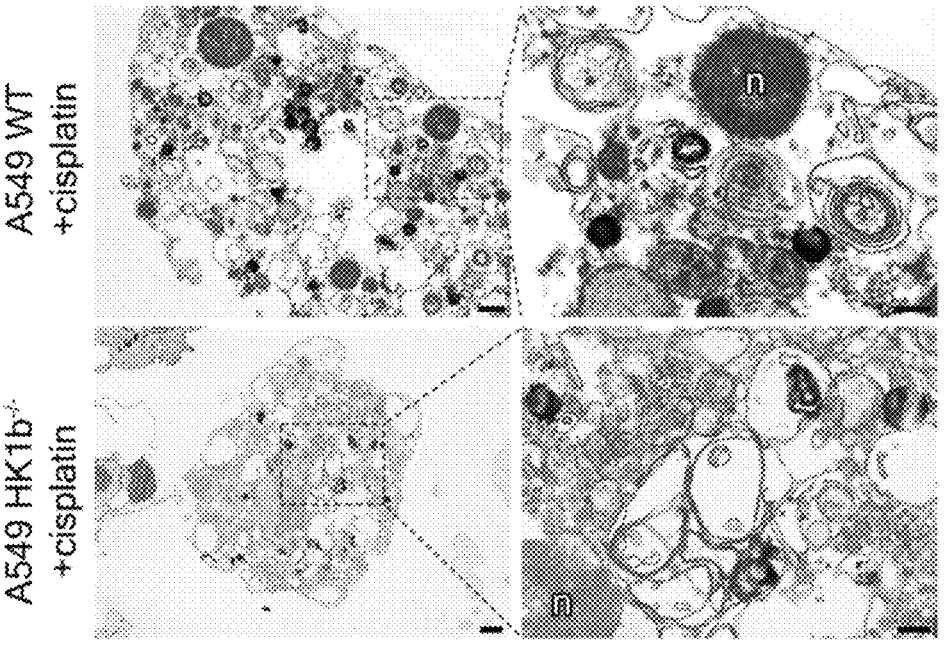

In order to identify the underlying mechanism of the effects of HK1b deletion and cisplatin treatment on synergistic induction of apoptosis, we examined the proliferation and survival signaling pathways. Upon silencing of HK1b, we observed that AKT activation and its downstream target GSK3β were activated, but they were totally inhibited in combination with cisplatin treatment. HK1b deletion and cisplatin together inhibit significantly phosphorylation of mTOR (FIG. 33), and STAT3 transcription factor (FIG. 32). Taken together these results indicate that, HK1b ablation and cisplatin down-regulate several oncogenic cascades: P13-kinase, and STAT pathways in NSCLC cells, revealing the underlying mechanism behind the inhibition of cancer cell proliferation, survival, and tumor growth pathways.

Figure 33:
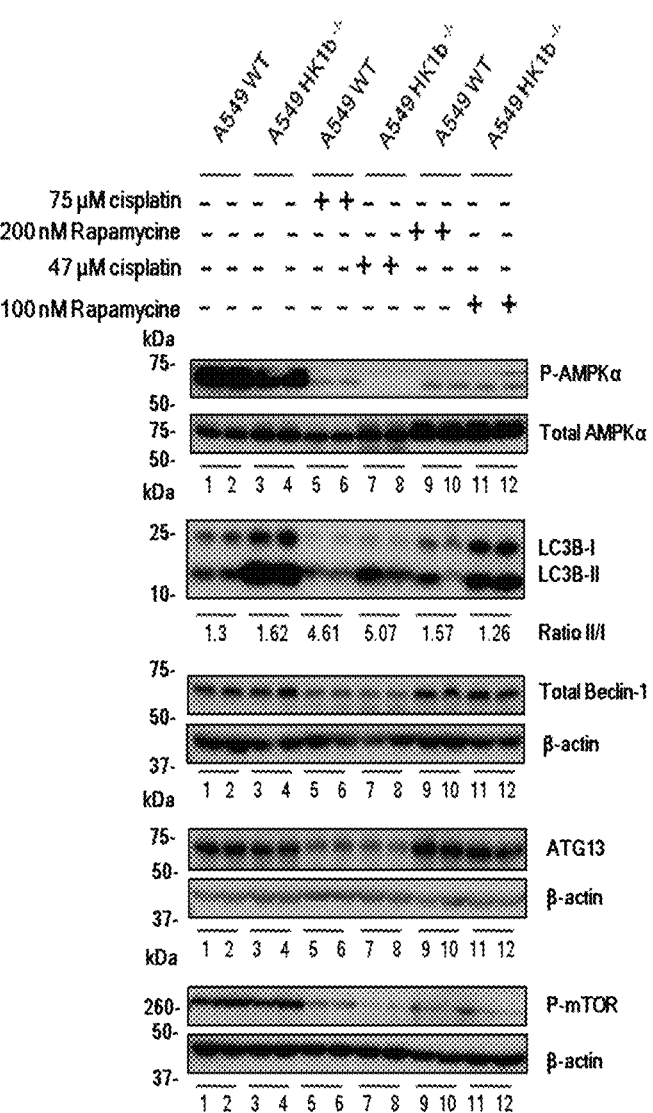
FIG. 33 depicts the immonoblot analysis of autophagic signaling pathway. HK1b elimination mitigates autophagy induction in response to glucose deprivation since formation of LC3II significantly elevated in A549 HK1b$^{-/-}$ cells. HK1b deletion and cisplatin inhibits significantly phosphorylation of mTOR in A549 HK1b$^{-/-}$ cells. Notably, these effects are not mediated by AMPK.
Figure 34:
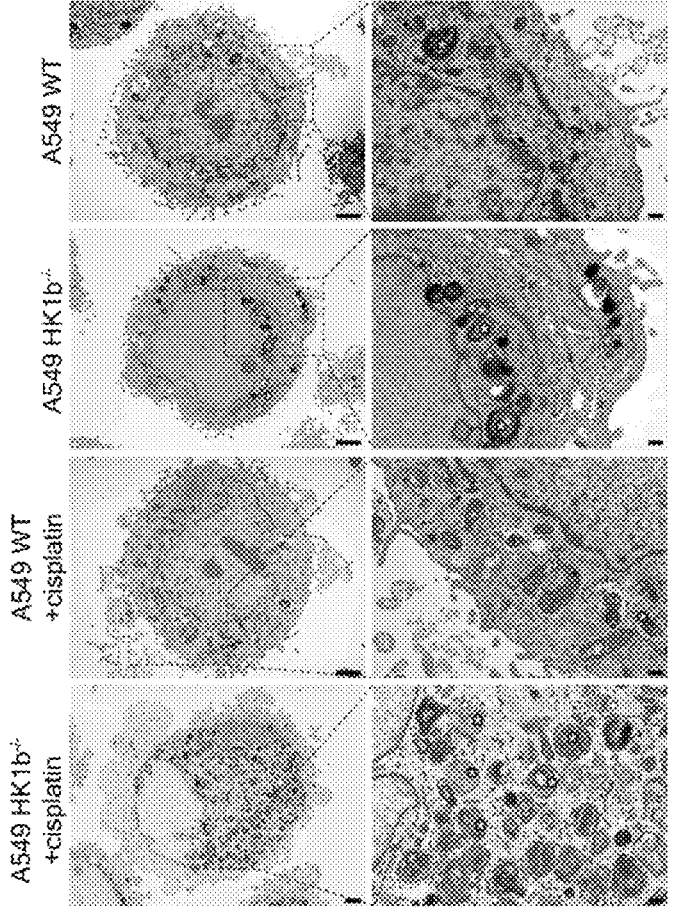
FIG. 34 depicts representative transmission electron microscopy (TEM) micrographs displaying characteristics of autophagy; images are representative of two independent experiments; scale bar, 2 μm (left) and 400 nm (right). Red arrows represent autophagic vesicles, black starts represent myelinoid bodies and n refers to nuclear fragment
Figure 35:
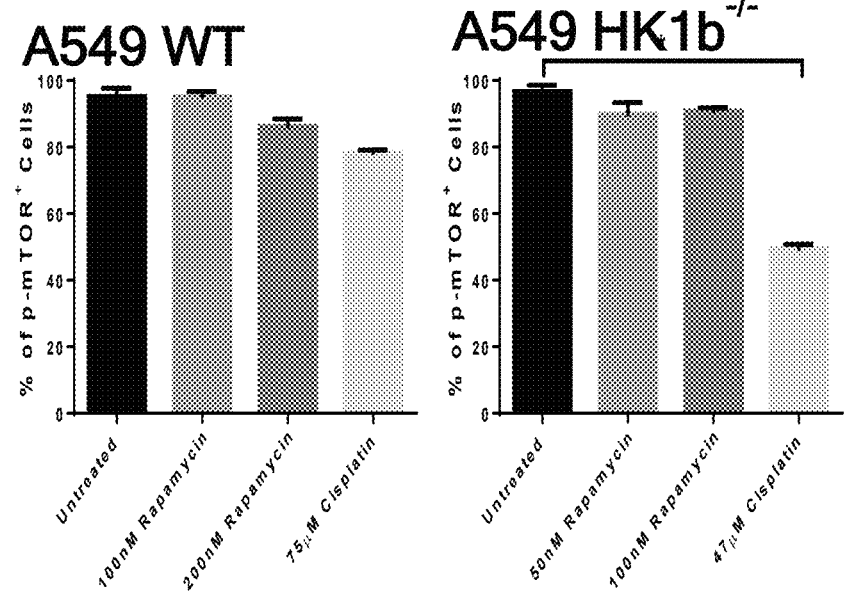
FIG. 35 depicts the flow cytometric analysis of mTOR activation shows that HK1b deletion and cisplatin significantly inhibits mTOR phosphorylation (p=0.001). Results are the mean+/–SD of 3 independent experiments. P-values were calculated using Student's t-test (*, P<0.001).
Figure 35:
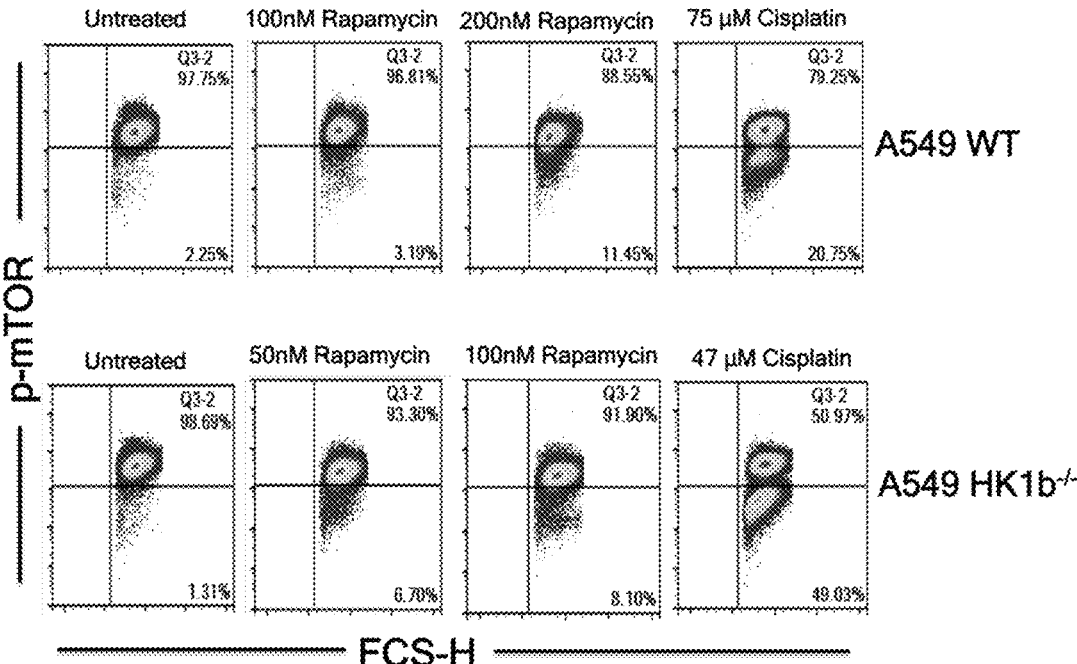
Figure 36:
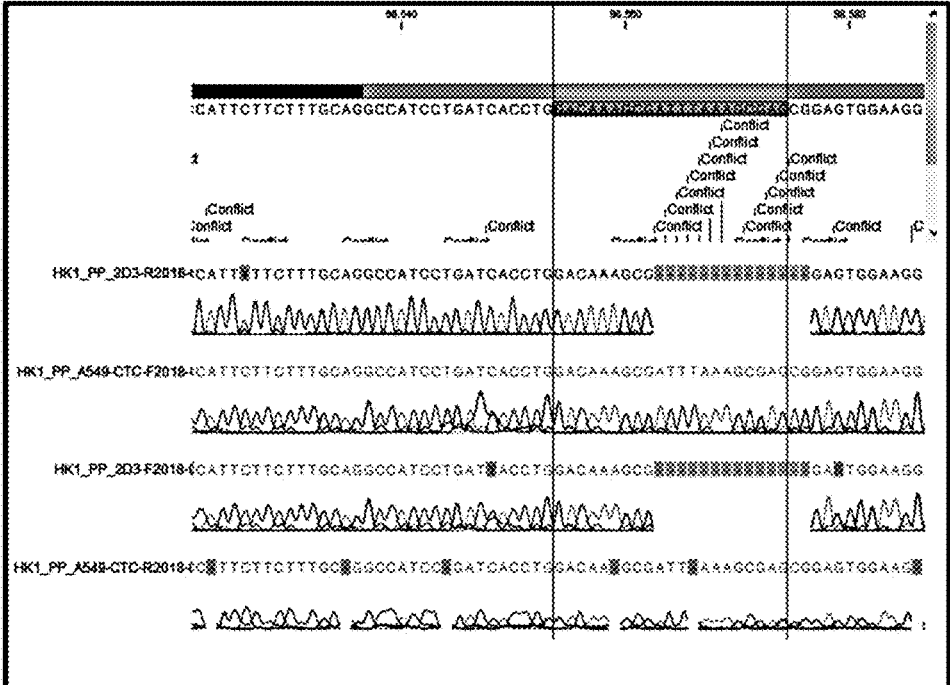
FIG. 36 depicts the results of sanger sequencing analysis. sgRNAs specific for HK1b isoform only was designed to target the eighth exon of human HK1 gene. pX458 vector with GFP selection marker The expression of GFP sorted single-cell clones expressing .sgHK1b was screened for HK1b isoform elimination and specific indel mutations at target loci was confirmed with PCR, and Sanger sequencing and HK1b showed deletion of 14 bp nucleotides in the target DNA.

E) Combination of HK1b Ablation and Cisplatin Synergistically Increases Both Apoptotic and Autophagic Cell Death We found that HK1b deletion sensitizes to cisplatin and in combination induce higher number of apoptotic cells. To investigate the underlying mechanism of cell death we examined the different cell death pathways of A549 WT and A549 HK1b$^{-/-}$ cells with cisplatin or rapamycin treatment. Furthermore, we showed that HK1b ablation and cisplatin increase apoptosis through both activation and high level of expression of p53. Recent studies have revealed a complex and multifaceted relationship between autophagy and apoptosis. Moreover, glucose deprivation typically results in autophagy induction to maintain energy homeostasis. In order to determine whether the combination of HK1b deletion and cisplatin led to the activation of autophagy in A549 cells, we examined the autophagic signaling pathway also using rapamycin treatment as a control. As expected, HK1b elimination mitigates autophagy induction in response to glucose deprivation since formation of LC3II significantly elevated in A549 HK1b$^{-/-}$ cells. Furthermore, HK1b deletion with cisplatin or rapamycin treatment induces greater autophagy in A549 HK1b⁻/⁻ cells. HK1b deletion and cisplatin inhibits phosphorylation of mTOR in A549 HK1b⁻/⁻ cells significantly (FIG. 33). Notably, these effects are not mediated by AMPK, since activity of this enzyme is not impacted by elimination of HK1b levels since phosphorylation of AMPK was not changed. Further, upon cisplatin or rapamycin treatment, AMPK phosphorylation was diminished in A549 WT cells but the phosphorylation totally inhibited A549 HK1b⁻/⁻ cells (FIG. 33). Although we observed higher LC3II expression level in cisplatin or rapamycin treated A549 HK1b⁻/⁻ cells, another autophagic indicators of beclin-1 and ATG13 expression levels were downregulated in both A549 WT, A549 HK1b⁻/⁻ cells. However, concomitantly beclin-1 and ATG13 levels were not changed with rapamycin treatment We further demonstrate that HK1b deletion and cisplatin induce significant numbers of autophagic vesicles and myelinoid bodies as indicated with electron microscopy (EM). Altogether we demonstrate that autophagy was induced mainly by reduction of glycolysis and apoptotic cell death was induced mainly by cisplatin. These data imply that combination of HK1b deletion with cisplatin induce greater cell death through increase activity of apoptotic and autophagic pathways.

REFERENCES

1. Douglas hanahan & robert weinberg, cell, hallmarks of cancer The next generation Volume 144, Issue 5, 4 Mar. 2011, Pages 646-674
2. Understanding the Warburg Effect: The Metabolic Requirements of Cell Proliferation: Science. 2009 May 22; 324(5930): 1029-1033. doi:10.1126/science.1160809
3. Targeting Metabolism for Cancer Therapy-cell-Alba Luengo.
4. Goodwin, J., et al., *The distinct metabolic phenotype of lung squamous cell carcinoma defines selective vulnerability to glycolytic inhibition.* Nat Commun, 2017. 8: p. 15503.
5. Anna M. Puzio-Kuter. Genes & Cancer. 2011; 2(4), 385-391
6. Vousden, K and Ryan, K. Nature Reviews Cancer. 2009; 9, 691-700
7. Mathupala, et al. Oncogene. 2006; 25, 4777-4786
8. Subcellular Localization of Hexokinases I and II Directs the Metabolic Fate of Glucose-Plos one
9. Robey R B, Hay N. Mitochondrial hexokinases, novel mediators of the antiapoptotic effects of growth factors and Akt. Oncogene 2006; 25(34):4683-96 doi 10.1038/sj.onc.1209595.
10. Rose I A, Warms J V. Mitochondrial hexokinase. Release, rebinding, and location. The Journal of biological chemistry 1967; 242(7):1635-45.
11. Testis-Specific Expression of mRNAs for a Unique Human Type 1 Hexokinase Lacking the Porin-Binding Domain
12. Mori C, Welch J E, Fulcher K D, O'Brien D A, Eddy E M (1993): Unique hexokinase messenger ribonucleic acids lacking the porin-binding domain are developmentally expressed in mouse spermatogenic cells. Biol Reprod 49:191-203.

The invention claimed is:

1. Double stranded molecules for inhibiting the expression of HK1b isoform when introduced in a cell, comprising a sense strand and an antisense strand, wherein the sense strand comprises a nucleotide sequence corresponding to SEQ ID No:1 and an antisense strand comprises a nucleotide sequence corresponding to SEQ ID No:4, wherein the sense strand comprises a nucleotide sequence corresponding to SEQ ID No:2 and an antisense strand comprises a nucleotide sequence corresponding to SEQ ID No:5, or wherein the sense strand comprises a nucleotide sequence corresponding to SEQ ID No:3 and an antisense strand comprises a nucleotide sequence corresponding to SEQ ID No:6.

2. A double stranded molecule according to claim 1 for use as a medicament.

3. A double stranded molecule according to claim 1 for use in prophylaxis and/or treatment of cancer.

4. A double stranded molecule according to claim 1 in combination with a chemotherapy agent selected from a group comprising cisplatin, carboplatin, oxaliplatin for use in prophylaxis and/or treatment of cancer.

5. A pharmaceutical composition comprising a double stranded molecule according to claim 1 and at least one pharmaceutically acceptable excipient.

* * * * *

SEQUENCE LISTING

<160> NUMBER OF SEQ ID NOS: 8

<210> SEQ ID NO 1
<211> LENGTH: 23
<212> TYPE: RNA
<213> ORGANISM: Artificial Sequence
<220> FEATURE:
<223> OTHER INFORMATION: siRNA #1

<400> SEQUENCE: 1
aagcgauuua aagcgagcgg auu                                    23

<210> SEQ ID NO 2
<211> LENGTH: 23
<212> TYPE: RNA
<213> ORGANISM: Artificial Sequence
<220> FEATURE:
<223> OTHER INFORMATION: siRNA #2 sense

<400> SEQUENCE: 2
aaagcgauuu aaagcgagcg guu                                    23

<210> SEQ ID NO 3
<211> LENGTH: 22
<212> TYPE: RNA
<213> ORGANISM: Artificial Sequence
<220> FEATURE:
<223> OTHER INFORMATION: siRNA #3 sense

<400> SEQUENCE: 3
gcgauuuaaa gcgagcggag uu                                     22

<210> SEQ ID NO 4

-continued

```
<211> LENGTH: 23
<212> TYPE: RNA
<213> ORGANISM: Artificial Sequence
<220> FEATURE:
<223> OTHER INFORMATION: siRNA #1 antisense

<400> SEQUENCE: 4
uccgcucgcu uuaaaucgcu uuu                                                    23

<210> SEQ ID NO 5
<211> LENGTH: 23
<212> TYPE: RNA
<213> ORGANISM: Artificial Sequence
<220> FEATURE:
<223> OTHER INFORMATION: siRNA #2 antisense

<400> SEQUENCE: 5
ccgcucgcuu uaaaucgcuu uuu                                                    23

<210> SEQ ID NO 6
<211> LENGTH: 23
<212> TYPE: RNA
<213> ORGANISM: Artificial Sequence
<220> FEATURE:
<223> OTHER INFORMATION: siRNA #3 antisense

<400> SEQUENCE: 6
aaagcgauuu aaagcgagcg guu                                                    23

<210> SEQ ID NO 7
<211> LENGTH: 20
<212> TYPE: DNA
<213> ORGANISM: Artificial Sequence
<220> FEATURE:
<223> OTHER INFORMATION: HK1b isoform Sense

<400> SEQUENCE: 7
gcgatttaaa gcgagcggag                                                       20

<210> SEQ ID NO 8
<211> LENGTH: 20
<212> TYPE: DNA
<213> ORGANISM: Artificial Sequence
<220> FEATURE:
<223> OTHER INFORMATION: HK1b isoform antisense

<400> SEQUENCE: 8
ctccgctcgc tttaaatcgc                                                       20
```